United States Patent
Ben-Asher et al.

(10) Patent No.: US 11,471,448 B2
(45) Date of Patent: Oct. 18, 2022

(54) SPHINGOSINE KINASE 2 INHIBITOR FOR TREATING CORONAVIRUS INFECTION IN MODERATELY SEVERE PATIENTS WITH PNEUMONIA

(71) Applicant: RedHill Biopharma Ltd., Tel-Aviv (IL)

(72) Inventors: Dror Ben-Asher, Tel-Aviv (IL); Reza Fathi, Oradell, NJ (US); Mark Levitt, Hashmonaim (IL); Ofra Barnett, Tel-Aviv (IL)

(73) Assignee: RedHill Biopharma Ltd., Tel-Aviv (IL)

( * ) Notice: Subject to any disclaimer, the term of this patent is extended or adjusted under 35 U.S.C. 154(b) by 0 days.

(21) Appl. No.: 17/552,038

(22) Filed: Dec. 15, 2021

(65) Prior Publication Data

US 2022/0184053 A1 Jun. 16, 2022

Related U.S. Application Data

(60) Provisional application No. 63/125,427, filed on Dec. 15, 2020.

(51) Int. Cl.
*A61K 31/4409* (2006.01)
*A61K 9/48* (2006.01)
*A61P 31/14* (2006.01)

(52) U.S. Cl.
CPC ............ *A61K 31/4409* (2013.01); *A61K 9/48* (2013.01); *A61P 31/14* (2018.01)

(58) Field of Classification Search
CPC ........ A61K 31/4409; A61K 9/48; A61P 31/14
USPC .......................................................... 514/43
See application file for complete search history.

(56) References Cited

U.S. PATENT DOCUMENTS

| | | |
|---|---|---|
| 6,624,169 B1 | 9/2003 | Wilhelm et al. |
| 6,861,435 B2 | 3/2005 | Ziegler |
| 7,211,670 B2 | 5/2007 | Ziegler et al. |
| 7,247,724 B2 | 7/2007 | Wosikowski-Buters et al. |
| 7,338,961 B2 | 3/2008 | Smith et al. |
| 7,342,018 B2 | 3/2008 | Wilhelm et al. |
| 7,608,623 B2 | 10/2009 | Sperl et al. |
| 7,659,396 B2 | 2/2010 | Wosikowski-Buters et al. |
| 7,713,980 B2 | 5/2010 | Grunenberg et al. |
| 7,745,441 B1 | 6/2010 | Wikstrom et al. |
| 7,807,681 B2 | 10/2010 | Sperl et al. |
| 7,884,206 B2 | 2/2011 | Ziegler et al. |
| 7,951,943 B2 | 5/2011 | Greiving |
| 8,063,248 B2 | 11/2011 | Smith et al. |
| 8,324,237 B2 | 12/2012 | Smith et al. |
| 8,492,385 B2 | 7/2013 | Grunenberg et al. |
| 8,557,800 B2 | 10/2013 | Smith et al. |
| 8,642,761 B2 | 2/2014 | Ziegler et al. |
| 9,089,532 B2 | 7/2015 | Schmalix et al. |
| RE46,424 E | 6/2017 | Ziegler et al. |
| 9,687,477 B2 | 6/2017 | Hahm et al. |
| 11,052,073 B1 * | 7/2021 | Ben-Asher ............... A61K 9/48 |

| | | |
|---|---|---|
| 2008/0066198 A1 | 4/2008 | Owens et al. |
| 2016/0082074 A1 | 3/2016 | Naoumov et al. |
| 2018/0125831 A1 | 5/2018 | Fathi et al. |

FOREIGN PATENT DOCUMENTS

WO  2020/076760 A2  4/2020

OTHER PUBLICATIONS

Glossary of medical education terms, Institute of International Medical Education. http://www.iime.org/glossary.htm Accessed in Mar. 2013. (Year: 2013).*
McGowan et al. Targeting the SphK-S1P-S1PR Pathway as a Potential Therapeutic Approach for COVID-19. Int. J. Mol. Sci. 2020, 21, 7189; doi:10.3390/ijms21197189 (Year: 2020).*
ClinicalTrials.gov Identifier: NCT04414618. A Study of Opaganib in Coronavirus Disease 2019 Pneumonia (COVID-19). First Posted: Jun. 4, 2020. (Year: 2020).*
Sundaramoorthy et al. The combination of a sphingosine kinase 2 inhibitor (ABC294640) and a Bcl-2 inhibitor (ABT-199) displays. Cancer Medicine. 2018;7:3257-3268. (Year: 2018).*
Hofmann et al., "Susceptibility to SARS coronavirus S protein-driven infection correlated with expression of angiotensin converting enzyme 2 and infection can be blocked by soluble receptor", Biochemical and Biophysical Research Communication 319 (2004) 1216-1221.
Hoffmann et al. "Nafamostat Mesylate Blocks Activation of SARS-CoV-2: New Treatment for COVID-19". Antimicrobial Agents and Chemotherapy, vol. 64, Issue 6 (2020) 1-3.
Hoffmann et al. "SARS-CoV-2 Cell Entry Depends on ACE2 and TMPRSS2 and is Blocked by a Clinically Proven Protease Inhibitor." Cell 181 (2020) 1-10.
Shen et al. "TMPRSS2: A potential target for treatment of influenza virus and coronavirus infection." Biochimie 142 (2017) 1-10.
Huggins "Structural analysis of experimental drugs binding to SARS-CoV-2 target TMPRSS2" Journal of Molecular Graphics and Modelling 100 (2020) 1-7.
Wang et al. "A Unique Protease Cleavage Site Predicted in the Spike Protein of the Novel Pneumonia Coronavirus (2019-nCoV) Potentially Related to Viral Transmissibality" Virologica Sinica (2020) 35:337-339.
Ebenzer et al. "Pseudomonas aeruginosa stimulates nuclear sphingosine-1-phosphate generation and epigentic regulation of lung inflammatory injury" Thorax 74(6) (2019): 579-591.
Al-Shujairi et al. "In vitro and in vivo roles of sphingosine kinase 2 during dengue virus infection" Journal of General Virology, 100 (2019): 629-641.
Reid et al. "Sphingosine kinase 2 is a chikungunya virus host factor co-localized with the viral replication complex". Emerging Microbes and Infections 4 (2015): 1-9.
Meacci et al. "SARS-CoV-2 Infection: A Role for S1P/S1P Receptor Signaling in the Nervous System?" International Journal of Molecular Sciences. 21, 6773 (2020). 1-18.

(Continued)

*Primary Examiner* — Yih-Horng Shiao
(74) *Attorney, Agent, or Firm* — Greenberg Traurig, LLP

(57) ABSTRACT

The disclosure is directed to ABC294640, as free base or as salts thereof, in preparing medicines for treating coronavirus infection or preventing diseases caused by coronavirus infection, and a medicine for preventing coronavirus infection or preventing diseases caused by coronavirus infection.

20 Claims, 8 Drawing Sheets

(56) References Cited

OTHER PUBLICATIONS

Studstill et al. "Sphingosine kinase 2 restricts T cell immunopathology but permits viral persistence" J Clin Invest: 130(12) (2020): 6523-6538.

Xia et al. "Transient inhibition of sphingosine kinases confers protection to influenza A virus infected mice" Antiviral Research 158 (2018): 171-177.

International Search Report and Written Opinion from International Application No. PCT/IB2021/000131 dated Aug. 6, 2021.

Sundaramoorthy et al., "The combination of a sphingosine kinase 2 inhibitor (ABC294640) and a Bcl-2 inhibitor (ABT-199) displays synergistic anti-myeloma effects in myeloma cells without a t(11;14) translocation", Cancer Medicine, 2018; 7: 3257-3268.

El Baira et al., "Repurposing anticancer drugs for the management of COVID-19", European Journal of Cancer, 141 (2020) 40-61.

\* cited by examiner

SPHINGOSINE KINASE 2 INHIBITOR FOR TREATING CORONAVIRUS INFECTION IN MODERATELY SEVERE PATIENTS WITH PNEUMONIA

CROSS-REFERENCE TO RELATED APPLICATIONS

This application claims the benefit of and priority to U.S. Provisional 63/125,427, filed Dec. 15, 2020, the entire content of which is hereby incorporated by reference in its entirety.

BACKGROUND

Coronaviruses are lipid enveloped positive-stranded RNA viruses (+ss RNA) that replicate in the cell cytoplasm. Prior to 2002, coronaviruses were not considered to be significant human pathogens. Other human coronaviruses such as HCoV-229E and HCoV-OC43 resulted in only mild respiratory infections in healthy adults. In 2002, however, severe acute respiratory syndrome coronavirus (SARS-CoV) emerged in Guangdong Province, China. While SARS-CoV predominantly impacted Southeast Asia, with significant outbreaks throughout China, Hong Kong, Taiwan, Singapore, and Vietnam, the virus was carried outside the region.

In 2012, Middle East respiratory syndrome coronavirus (MERS-CoV), was detected in a patient with severe respiratory disease in Saudi Arabia. The clinical features of MERS-CoV infection in humans range from asymptomatic to very severe pneumonia with the potential development of acute respiratory distress syndrome, septic shock, and multiorgan failure resulting in death. Since the first case of MERS-CoV infection was reported and the virus was isolated, significant progress has been made toward understanding the epidemiology, ecology, and biology of the virus. Several assays for the detection of acute infection with MERS-CoV by real-time reverse transcription (RT)-PCR have been developed and are in widespread use.

In 2019, a novel coronavirus (nCoV) emerged in the world and is now known to cause coronavirus disease 2019 (COVID-19). COVID-19 is an infectious disease caused by severe acute respiratory syndrome coronavirus 2 (SARS coronavirus-2 or SARS-CoV-2), a virus phylogenetically closely related to SARS virus. The World Health Organization (WHO) has declared the 2019-2020 coronavirus outbreak to be a Public Health Emergency of International Concern (PHEIC). For most patients, COVID-19 begins and ends in their lungs, because coronaviruses primarily cause respiratory diseases.

SUMMARY

The present invention relates generally to the fields of virology, infectious disease and medicine. The invention provides a new use of ABC294640 as free bases or as salts thereof in the preparation of medicines for treating coronavirus infection in humans.

According to aspects illustrated herein, there is disclosed a method for the treatment of a disease caused by a coronavirus, the method comprising confirming a patient is infected with a coronavirus and also has pneumonia; assessing that the patient requires supplemental oxygen at most at a fraction of inspired oxygen (FiO2) up to and including 60%; and administering to the patient an effective amount of ABC294640,

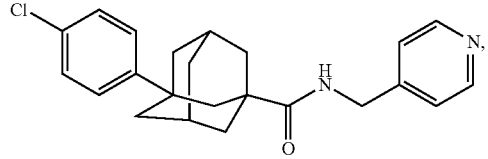 [SMILES: O=C(NCc1ccncc1)C12CC3CC(C1)CC(c1ccc(Cl)cc1)(C3)C2]

as a free base or as a salt thereof. In an embodiment, ABC294640 exists as a hydrochloride salt. In an embodiment, the ABC294640 is in combination with a pharmaceutically-acceptable carrier material. In an embodiment, the pharmaceutically-acceptable carrier material is physiologically buffered saline. In an embodiment, a suspension is formed that includes ABC294640 hydrochloride suspended in physiologically buffered saline and administering includes using a tube to deliver the suspension directly to the stomach. In an embodiment, the ABC294640 and optionally the pharmaceutically-acceptable carrier material, are in a unit dosage form suitable for oral administration. In an embodiment, the unit dosage form is a solid dosage form. In an embodiment, the solid dosage form is a capsule. In an embodiment, the patient is receiving oxygen via nasal cannula. In an embodiment, the coronavirus is a respiratory syndrome coronavirus. In an embodiment, the respiratory syndrome coronavirus is a severe acute respiratory syndrome coronavirus. In an embodiment, the severe acute respiratory syndrome coronavirus is severe acute respiratory syndrome coronavirus-2 (SARS-CoV-2). In an embodiment, the SARS-CoV-2 virus is wild-type. In an embodiment, the SARS-CoV-2 virus is a naturally occurring coronavirus variant. In an embodiment, the unit dosage form suitable for oral administration is a capsule having 250 mg of ABC294640 hydrochloride, and wherein administering includes two capsules administered twice a day, for at least 10 days, for a total daily dose of 1000 mg of ABC294640 hydrochloride.

According to aspects illustrated herein, there is disclosed a method for the treatment of the 2019 coronavirus disease (COVID-19) caused by the SARS-CoV-2 virus, that includes administering to a person in need thereof an effective amount of ABC294640,

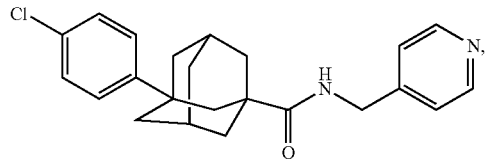 [SMILES: O=C(NCc1ccncc1)C12CC3CC(C1)CC(c1ccc(Cl)cc1)(C3)C2]

as a free base or as a salt thereof. In an embodiment, ABC294640 exists as a hydrochloride salt. In an embodiment, the ABC294640 is in combination with a pharmaceutically-acceptable carrier material. In an embodiment, the pharmaceutically-acceptable carrier material is physiologically buffered saline. In an embodiment, a suspension is formed that includes ABC294640 hydrochloride suspended in physiologically buffered saline and administering includes using a tube to deliver the suspension directly to the stomach. In an embodiment, the ABC294640 and optionally the pharmaceutically-acceptable carrier material, are in a unit dosage form suitable for oral administration. In an embodiment, the unit dosage form is a solid dosage form. In an embodiment, the solid dosage form is a capsule. In an embodiment, the SARS-CoV-2 virus is wild-type. In an embodiment, the SARS-CoV-2 virus is a naturally occurring coronavirus variant. In an embodiment, the unit dosage form suitable for oral administration is a capsule having 250 mg of ABC294640 hydrochloride, and wherein administering includes two capsules administered twice a day, for at least 10 days, for a total daily dose of 1000 mg of ABC294640 hydrochloride.

According to aspects illustrated herein, there is disclosed a method of treatment comprising administering an effective amount of ABC294640,

[Chemical structure: 3-(4-chlorophenyl)-adamantane-1-carboxylic acid (pyridin-4-ylmethyl)-amide]

as a free base or as a salt thereof, to a human having 2019 coronavirus disease (COVID-19) caused by the SARS-CoV-2 virus. In an embodiment, ABC294640 exists as a hydrochloride salt. In an embodiment, the ABC294640 is in combination with a pharmaceutically-acceptable carrier material. In an embodiment, the pharmaceutically-acceptable carrier material is physiologically buffered saline. In an embodiment, a suspension is formed that includes ABC294640 hydrochloride suspended in physiologically buffered saline and administering includes using a tube to deliver the suspension directly to the stomach. In an embodiment, the ABC294640 and optionally the pharmaceutically-acceptable carrier material, are in a unit dosage form suitable for oral administration. In an embodiment, the dosage form is a solid dosage form. In an embodiment, the solid dosage form is a capsule. In an embodiment, the SARS-CoV-2 virus is wild-type. In an embodiment, the SARS-CoV-2 virus is a naturally occurring coronavirus variant. In an embodiment, the unit dosage form suitable for oral administration is a capsule having 250 mg of ABC294640 hydrochloride, and wherein administering includes two capsules administered twice a day, for at least 10 days, for a total daily dose of 1000 mg of ABC294640 hydrochloride.

According to aspects illustrated herein, there is disclosed ABC294640,

[Chemical structure]

as a free base or as a salt thereof, for use in treating coronavirus infection.

According to aspects illustrated herein, there is disclosed ABC294640,

[Chemical structure]

as a free base or as a salt thereof, for use in treating the 2019 coronavirus disease (COVID-19) caused by the SARS-CoV-2 virus.

According to aspects illustrated herein, there is disclosed (3-(4-Chloro-phenyl)-adamantane-1-carboxylic acid(pyridin-4-ylmethyl)-amide), as a free base or as a salt thereof, for use in treating coronavirus infection.

According to aspects illustrated herein, there is disclosed (3-(4-Chloro-phenyl)-adamantane-1-carboxylic acid(pyridin-4-ylmethyl)-amide), as a free base or as a salt thereof, for use in treating the 2019 coronavirus disease (COVID-19) caused by the SARS-CoV-2 virus.

According to aspects illustrated herein, there is disclosed use of ABC294640,

[Chemical structure]

as a free base or as a salt thereof, for the manufacture of a medicament for treatment of coronavirus infection.

According to aspects illustrated herein, there is disclosed use of ABC294640,

[Chemical structure]

as a free base or as a salt thereof, for the manufacture of a medicament for treatment of the 2019 coronavirus disease (COVID-19) caused by the SARS-CoV-2 virus.

According to aspects illustrated herein, there is disclosed use of (3-(4-Chloro-phenyl)-adamantane-1-carboxylic acid (pyridin-4-ylmethyl)-amide), as a free base or as a salt thereof, for the manufacture of a medicament for treatment of coronavirus infection.

According to aspects illustrated herein, there is disclosed use of compound (3-(4-Chloro-phenyl)-adamantane-1-carboxylic acid(pyridin-4-ylmethyl)-amide), as a free base or as a salt thereof, for the manufacture of a medicament for treating the 2019 coronavirus disease (COVID-19) caused by the SARS-CoV-2 virus.

According to aspects illustrated herein, there is disclosed a pharmaceutical composition for the treatment of coronavirus infection, comprising ABC294640,

[Chemical structure]

as a free base or as a salt thereof, and optionally a pharmaceutically-acceptable carrier material.

According to aspects illustrated herein, there is disclosed a pharmaceutical composition for the treatment of the 2019 coronavirus disease (COVID-19) caused by the SARS-CoV-2 virus, comprising ABC294640,

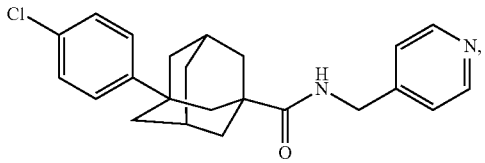 [SMILES: O=C(NCc1ccncc1)C12CC3CC(C1)CC(c1ccc(Cl)cc1)(C3)C2]

as a free base or as a salt thereof, and optionally a pharmaceutically-acceptable carrier material.

According to aspects illustrated herein, there is disclosed a pharmaceutical composition for the treatment of coronavirus infection, comprising (3-(4-Chloro-phenyl)-adamantane-1-carboxylic acid(pyridin-4-ylmethyl)-amide), as a free base or as a salt thereof, and optionally a pharmaceutically-acceptable carrier material.

According to aspects illustrated herein, there is disclosed a pharmaceutical composition for the treatment of the 2019 coronavirus disease (COVID-19) caused by the SARS-CoV-2 virus, comprising (3-(4-Chloro-phenyl)-adamantane-1-carboxylic acid(pyridin-4-ylmethyl)-amide), as a free base or as a salt thereof, and optionally a pharmaceutically-acceptable carrier material.

According to aspects illustrated herein, there is disclosed an anti-coronavirus infection agent comprising ABC294640,

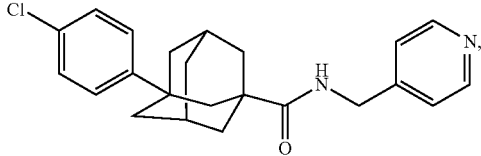 [SMILES: O=C(NCc1ccncc1)C12CC3CC(C1)CC(c1ccc(Cl)cc1)(C3)C2]

as a free base or as a salt thereof.

According to aspects illustrated herein, there is disclosed an anti-coronavirus infection agent comprising (3-(4-Chloro-phenyl)-adamantane-1-carboxylic acid(pyridin-4-ylmethyl)-amide), as a free base or as a salt thereof.

According to aspects illustrated herein, there is disclosed a method for the treatment of human coronavirus infection, comprising administering to a subject in need thereof a therapeutically effective amount of ABC294640 (3-(4-Chloro-phenyl)-adamantane-1-carboxylic acid(pyridin-4-ylmethyl)-amide) or a pharmaceutically acceptable salt thereof. In an embodiment, the method further comprises diagnostically confirming that the subject is infected with a human coronavirus prior to administering ABC294640. In an embodiment, ABC294640 exists as a hydrochloride salt. In an embodiment, the coronavirus infection is severe acute respiratory syndrome coronavirus 2 (SARS-CoV-2).

According to aspects illustrated herein, there is disclosed a method of treating COVID-19 (SARS-CoV-2) coronavirus infection, the method comprising administering to a subject in need thereof for at least 10 days one or more therapeutically effective doses of ABC294640 (3-(4-Chloro-phenyl)-adamantane-1-carboxylic acid(pyridin-4-ylmethyl)-amide) or a pharmaceutically acceptable salt thereof. In an embodiment, the method further comprises diagnostically confirming that the subject is infected with SARS-CoV-2 prior to administering ABC294640. In an embodiment, ABC294640 exists as a hydrochloride salt. In an embodiment, the total dose of ABC294640 per day is independently selected upon each occurrence from about 250 mg to about 1500 mg.

According to aspects illustrated herein, there is disclosed a method for treating COVID-19 (SARS-CoV-2) coronavirus infection, comprising administering to a human subject in need thereof a therapeutically acceptable amount of ABC294640 (3-(4-Chloro-phenyl)-adamantane-1-carboxylic acid(pyridin-4-ylmethyl)-amide) or a pharmaceutically acceptable salt thereof, ABC294640 having the ability to act on a host cell factor, sphingosine kinase-2 (SK2), which is involved in both viral replication inside the cell and downstream inflammatory/immune responses.

According to aspects illustrated herein, there is disclosed a method of modulating replication of coronavirus in a host cell infected with the coronavirus comprising administering to the host cell ABC294640 as a free base or as a salt thereof, in an amount effective to modulate replication of the virus.

According to aspects illustrated herein, there is disclosed use of ABC294640 as a free base or as a salt thereof in the preparation of drugs for treating coronavirus infection. In an embodiment, the coronavirus is a 2019 novel coronavirus COVID-19. In an embodiment, the coronavirus infection is coronavirus pneumonia. In an embodiment, ABC294640 exists as a hydrochloride salt. In an embodiment, the ABC294640 is active against a host cell factor, sphingosine inase-2, which is involved in both viral replication inside the cell and downstream inflammatory/immune responses.

According to aspects illustrated herein, the present invention features a packaged pharmaceutical product. The packaged pharmaceutical product includes a container, a plurality of ABC294640 unit dosage forms suitable for oral administration in the container, and a legend (e.g., a label or an insert) associated with the container and indicating administration of ABC294640 for treating 2019 coronavirus disease (COVID-19) caused by the SARS-CoV-2 virus.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

DEFINITIONS

Figure 1:
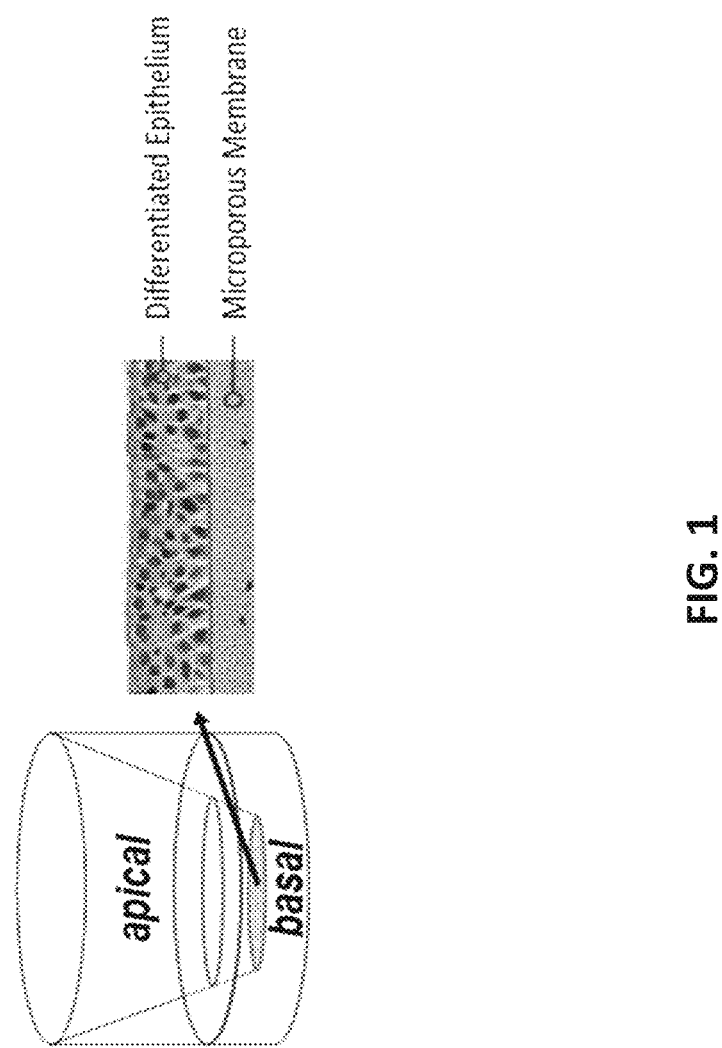
FIG. 1 is a depiction of the human EpiAirway™ cell culture model, herein referred to as human bronchial epithelial cells (HBEC).

As used herein, the term "agent" refers to a drug substance having pharmacological activity—an effect of the agent on an individual. The terms "agent," "active ingredient", "drug substance," and "compound" are used interchangeably herein.

As us herein, the term ABC294640 refers to [3-(4-chlorophenyl)-adamantane-1-carboxylic acid (pyridin-4-ylmethyl)amide] in a form as a free base or salt, or in stereoisomeric or non-stereoisomeric form. In the case of compounds, salts, prodrugs or solvates that are solids, it is understood by those skilled in the art that the inventive compounds, salts, and solvates may exist in different crystal forms, all of which are intended to be within the scope of the present invention. Opaganib, also known as ABC294640 hydrochloride, is a specific salt form of ABC294640.

As used herein, the term "coronavirus" includes naturally occurring (e.g. wild-type) coronavirus; naturally occurring coronavirus variants; and coronavirus variants generated in the laboratory, including variants generated by selection, variants generated by chemical modification, and genetically modified variants (e.g., coronavirus modified in a laboratory by recombinant DNA methods). In an embodiment, a subject can be tested for a viral infection within a few days after symptoms begin, or after treatment according to the present disclosure, by collecting nasal secretions (nasal or nasopharyngeal (NP) swabs), throat (oropharyngeal) swab, blood, or other body fluid samples and testing the sample for detection of viral antigens or RNA in blood and other body fluids using, for example, an antigen-capture enzyme-linked immunosorbent assay (ELISA), using an IgM ELISA (to determine whether the subject has IgM antibodies), using an IgG ELISA (to determine whether the subject has IgG antibodies), using polymerase chain reaction (PCR), or by virus isolation. In an embodiment, the coronavirus is selected from the group consisting of Middle East respiratory syndrome (MERS), severe acute respiratory syndrome (SARS) and SARS-CoV-2.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The terms "co-administer," "coadministration," or "in combination" are used to describe the administration of a compound of the present invention in combination with at least one other antiviral active agent. The timing of the coadministration is best determined by the medical specialist treating the patient. It is sometimes desired that the agents be administered at the same time. Alternatively, the drugs selected for combination therapy may be administered at different times to the patient. Of course, when more than one viral or other infection or other condition is present, the present compounds may be combined with other agents to treat that other infection or condition as required.

As related to the present invention, the term "treatment", "treating", and the like, is defined as prior to prophylactic administration of the compounds in the methods described herein, prior to viral infection, or inhibiting viral activity after infection has occurred. In an embodiment, the term "treating" is meant to administer one or more compounds of the present invention to measurably inhibit the replication of a virus in vitro or in vivo, to measurably decrease the load of a virus in a cell in vitro or in vivo, or to reduce at least one symptom associated with having a CoV-mediated disease in a patient. Desirably, the inhibition in replication or the decrease in viral load is at least 10%, 15%, 20%, 25%, 30%, 35%, 40%, 45%, 50%, 55%, 60%, 65%, 70%, 75%, 80%, 85%, 90%, 95%, 97%, 98%, 99%, as determined using a suitable assay. Assays that monitor replication of viruses include, but are not limited to, cytopathic viral assays, reporter-virus and reporter-cell assays, viral replicon assays, and gene-targeted viral assays. Viral load testing can be carried out using nucleic acid amplification based tests (NATs or NAATs) and non-nucleic acid-based tests on blood plasma samples to determine the quantity of virus in a given volume including viral RNA levels in plasma and tissue and total viral DNA. Alternatively, in certain embodiments, treatment is observed by a trained physician as an appreciable or substantial relief of symptoms in a patient with a CoV-mediated disease. Typically, a decrease in viral replication is accomplished by reducing the rate of RNA polymerization, RNA translation, protein processing or modification, or by reducing the activity of a molecule involved in any step of viral replication (e.g., proteins or coded by the genome of the virus or host important for viral replication). In an embodiment, the term "treat" refers to the ability of a compound or compounds of the present invention to inhibit or suppress replication of a virus, such as an RNA virus. In an embodiment, the term "treat" refers to the ability of a compound or compounds of the present invention to inhibit the cytopathic effect during a RNA virus infection.

In some embodiments, an "effective amount" or "immune-stimulatory amount" of a compound of the invention is an amount which, when administered to a subject, is sufficient to engender a detectable immune response. In other embodiments, a "protective effective amount" of an immunogenic composition is an amount which, when administered to a subject, is sufficient to confer protective immunity upon the subject. In other embodiments, a "therapeutic effect amount" of a compound is an amount which, when administered to a subject, is sufficient to treat a viral infection, such as increase viral clearance.

As used herein, the term "fraction of inspired oxygen" or "FiO2" refers to an estimation of the oxygen content a person inhales, delivered in supplemental flow necessary to meet oxygenation goals, ideally targeting a peripheral oxygen saturation (SpO2) of between 90 and 96 percent. Typically <10 L/min will yield a FiO2 of up to 60%.

The agents and methods of the present invention may be utilized to treat a subject in need thereof. In certain embodiments, the subject is a mammal such as a human, or a non-human mammal. When administered to an animal, such as a human, the agent is preferably administered as a pharmaceutical composition comprising, for example, at least one agent of the invention with a substance or collection of substances capable of being combined with the at least one agent. The term "pharmaceutically-acceptable carrier materials" as used herein means a substance or collection of substances capable of being combined with an agent that is suitable for use in contact with the tissues of mammals for purposes of a therapeutic treatment in the mammals under anticipated exposure conditions. Pharmaceutically-acceptable carrier materials are well known in the art and include, for example, inert solid, semi-solid or liquid filler, diluent, encapsulating material. Pharmaceutically-acceptable carrier materials must, of course, be of sufficiently high purity and sufficiently low toxicity to render them suitable for administration to the human or lower animal being treated. The pharmaceutical composition can be in unit dosage form such as tablet, capsule (including sprinkle capsule and gelatin capsule), granule, powder, syrup, suppository, injection or the like.

The term "immune response" refers to a response of a cell of the immune system, such as a B-cell, T-cell, macrophage or polymorphonucleocyte, to a stimulus such as an antigen. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection).

By "more effective" is meant that a treatment exhibits greater efficacy, or is less toxic, safer, more convenient, or less expensive than another treatment with which it is being compared. Efficacy may be measured by a skilled practitioner using any standard method that is appropriate for a given indication.

As used herein, the term "a suitable period of time" refers to the period of time starting when a patient begins treatment for a diagnosis of coronavirus infection using a method of the present disclosure, throughout the treatment, and up until when the patient stops treatment due to either a reduction in symptoms associated with the coronavirus infection or due to a laboratory diagnosis indicating that the viral infection is under control. In an embodiment, a suitable period of time is one (1) week. In an embodiment, a suitable period of time is between one (1) week and two (2) weeks. In an embodiment, a suitable period of time is two (2) weeks. In an embodiment, a suitable period of time is between two (2) weeks and three (3) weeks. In an embodiment, a suitable period of time is three (3) weeks. In an embodiment, a suitable period of time is between three (3) weeks and four (4) weeks. In an embodiment, a suitable period of time is four (4) weeks. In an embodiment, a suitable period of time is between four (4) weeks and five (5) weeks. In an embodiment, a suitable period of time is five (5) weeks. In an embodiment, a suitable period of time is between five (5) weeks and six (6) weeks. In an embodiment, a suitable period of time is six (6) weeks. In an embodiment, a suitable period of time is between six (6) weeks and seven (7) weeks.

In an embodiment, a suitable period of time is seven (7) weeks. In an embodiment, a suitable period of time is between seven (7) weeks and eight (8) weeks. In an embodiment, a suitable period of time is eight (8) weeks.

As used herein, the term "cytopathic effects" refers to the changes in cell morphology due to a viral infection.

As used herein, the terms "cytopathogenesis" or "pathogenesis" includes inhibition of host cell gene expression and includes other cellular changes that contribute to viral pathogenesis in addition to those changes that are visible at the microscopic level.

The term "in vitro" as used herein refers to procedures performed in an artificial environment, such as for example, without limitation, in a test tube or cell culture system. The skilled artisan will understand that, for example, an isolate SK enzyme may be contacted with a modulator in an in vitro environment. Alternatively, an isolated cell may be contacted with a modulator in an in vitro environment.

The term "in vivo" as used herein refers to procedures performed within a living organism such as, without limitation, a human, monkey, mouse, rat, rabbit, bovine, equine, porcine, canine, feline, or primate.

DETAILED DESCRIPTION

The disclosure relates generally to the fields of virology, infectious disease, and medicine and describes compounds, compositions, methods and kits for the treatment of CoV-mediated disease, e.g., one caused by SARS-CoV-2, SARS, or MERS. In an embodiment, the compositions comprise ABC294640 and a pharmaceutically-acceptable carrier material. In an embodiment, the present disclosure provides a new use/application of opaganib in the preparation of medicines for treating coronavirus infection in humans.

More specifically, the invention relates to effective inhibitors of coronaviruses which can treat coronaviruses, including the 2019 novel coronavirus. The invention provides a new use of opaganib as an effective inhibitor of coronaviruses, and its application in the preparation of drugs for treating coronavirus infection in humans.

ABC294640, [3-(4-chlorophenyl)-adamantane-1-carboxylic acid (pyridin-4-ylmethyl)amide], is an orally-administered, sphingosine kinase 2 ("SphK2" or "SK2") inhibitor. ABC294640 is represented by the following structural formula:

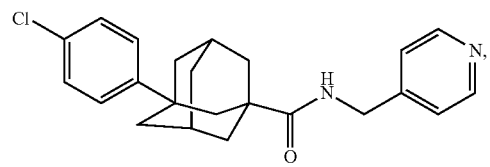 [SMILES: O=C(NCc1ccncc1)C12CC3CC(C1)CC(c1ccc(Cl)cc1)(C3)C2]

and can be prepared as a free base, in the form of its salts, and crystalline modifications. U.S. Pat. Nos. 7,338,961, 8,063,248, 8,324,237 and 8,557,800, which are incorporated herein by reference, teach these compounds, use, and methods of making same.

ABC294640 as the hydrochloride salt has been given an international nonproprietary name (INN) of opaganib and is represented by the following structural formula:

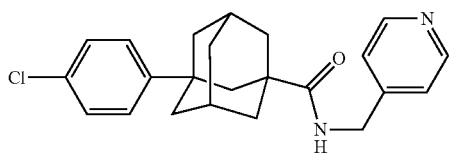

The molecular formula of opaganib is $C_{23}H_{25}ClN_2O \cdot HCl$ with a molecular mass of 417.4 g/mol. Opaganib is a non-hygroscopic, white to off-white solid which is practically insoluble in water and ethyl acetate. In an embodiment, a medicine is prepared by filling opaganib in hard gelatin size 1 capsules that further comprise at least one pharmaceutically-acceptable carrier material. In an embodiment, the pharmaceutically-acceptable carrier material are selected from the following excipients: microcrystalline cellulose; colloidal silicon dioxide; magnesium stearate vegetal; titanium dioxide. In an embodiment, opaganib capsules contain 250 mg ABC294640 as the hydrochloride salt or 228.16 mg of ABC294640 free base. In an embodiment, opaganib capsules contain 375 mg ABC294640 as the hydrochloride salt or 342.24 mg of ABC294640 free base.

In an embodiment, opaganib 250 mg capsules contain the agent ABC294640 as the hydrochloride salt along with excipients that are encapsulated in gelatin, white opaque body and cap, coni-snap capsules, size 1. In an embodiment, opaganib 375 mg capsules contain the agent ABC294640 as the hydrochloride salt along with excipients that are encapsulated in gelatin, white opaque body and cap, coni-snap capsules, size 1.

Opaganib for treating coronavirus infection is generally administered in an amount ranging from about 250 mg to about 1500 mg per day. In an embodiment, opaganib 250 mg is administered as two capsules, twice per day, for a total daily dose of 1000 mg. In an embodiment, opaganib 250 mg is administered as two capsules, 500 mg, Q12 hours. In an embodiment, a patient with a confirmed coronavirus infection is provided with instructions to take a single 500 mg dose of opaganib (as two 250 mg capsules) every 12 hours (so 1000 mg opaganib per day), for a total of up to 2 consecutive weeks, or up to consecutive 14 days.

The inventors have discovered the new use of opaganib after a lot of research. Opaganib has demonstrated antiviral, anti-inflammatory, and anti-thrombotic activity—acting on both the cause and the effects of COVID-19. Opaganib targets sphingosine kinase-2, a human cell component involved in viral replication and not the virus itself. The mounting evidence of new SARS-CoV-2 mutations emerging globally underscores the importance of this unique mechanism, which potentially minimizes the risk of viral resistance to therapy.

Provided herein are packaged pharmaceutical products, also known as pharmaceutical kits, that includes a container, a plurality of opaganib unit dosage forms suitable for oral administration in the container, and a legend (e.g., a label or an insert) associated with the container and indicating administration of opaganib for treating coronavirus infection. In an embodiment, the legend includes instructions for carrying out the methods described above and/or how to use the kit. Instructions included in the kit can be affixed as a label to packaging material or can be included as a package insert. While instructions are typically written or printed materials, they are not limited to such. Any medium capable of storing instructions and communicating them to an end user is contemplated by this disclosure. Such media include, but are not limited to, electronic storage media (e.g., magnetic discs, tapes, cartridges), optical media (e.g., CD ROM), and the like. As used herein, the term "instructions" can include the address of an internet site which provides instructions.

Combination and Alternation Therapy

The compounds described herein can be administered on top of the current standard of care for COVID patients, or in combination or alternation with any other compound or therapy that the healthcare provider deems beneficial for the patient. The combination and/or alternation therapy can be therapeutic, adjunctive, or palliative. When the methods include administering to a patient more than one active agent, the agents may be administered within 7, 6, 5, 4, 3, 2 or 1 days; within 24, 12, 6, 5, 4, 3, 2 or 1 hours, within 60, 50, 40, 30, 20, 10, 5 or 1 minutes; or substantially simultaneously. The methods of the invention may include administering one or more agents to the patient by oral, systemic, parenteral, topical, intravenous, inhalational, or intramuscular administration.

It has been observed that COVID patients can pass through various stages of disease, and that the standard of care can differ based on what stage of illness the patient presents with or advances to. COVID is noteworthy for the development of "cross-talk" between the immune system and the coagulation system. As the disease progresses, the patient can mount an overreaction by the immune system, which can lead to a number of serious implications, including a cytokine storm. Via the cross-talk between the immune system and the coagulation system, the patient can begin clotting in various areas of the body, including the respiratory system, brain, heart and other organs. Multiple clots throughout the body have been observed in COVID patients, requiring anticoagulant therapy. It is considered that these clots may cause long term, or even permanent damage if not treated and disease alleviated.

More specifically, COVID-19 has been described as progressing through three general stages of illness: stage 1 (early infection), stage 2 (pulmonary phase), and stage 3 (hyperinflammation phase/cytokine storm).

Stage 1 is characterized by non-specific, and often mild, symptoms. Viral replication is occurring, and it is appropriate to begin immediate treatment with the compounds described herein and perhaps in combination or alternation with another anti-viral therapy. Interferon-β may also be administered to augment the innate immune response to the virus. In one embodiment, therefore, a compound of the present invention is used in an effective amount in combination or alternation with interferon-β and or an additional anti-viral drug. Zinc supplements and or Vitamin C is also sometimes administered at this stage or as the illness progresses.

Stage 2 of COVID-19 is the pulmonary phase where patients may experience acute hypoxemic respiratory failure. In fact, the primary organ failure of COVID-19 is hypoxemic respiratory failure. It has been shown that moderate immunosuppression via a steroid, for example, dexamethasone, can be beneficial to patients with acute hypoxemic respiratory failure and/or patients on mechanical ventilation. In one embodiment, a compound the present invention is used in an effective amount in combination with a corticosteroid which may be a glucocorticoid. Non-limiting examples are the product budesonide sold under the trademark ENTOCORT EC, the product bethamethasone sold under the trademark CELESTONE, the product prednisone sold under the trademark INTENSOL, the product prednisolone sold under the trademarks ORAPED and PRE- LONE, the product triamcinolone sold under the trademarks ARISTOSPAN, INTRA-ARTICULAR, INTRALESIONAL and KENALOG, the product methylprednisolone sold under the trademarks MEDROL, DEPO-MEDROL and SOLU-MEDROL, hydrocortisone, or dexamethasone sold under the trademarks INTENSOL and DEXPAK.

The NS5B inhibitor Remdesivir has provided mixed results when given to COVID19 patients. It can only be administered in a hospital setting, and only by intravenous injection, typically three times a day, which makes it inappropriate for mild to moderate COVID19 patients. In one embodiment, a compound of the present invention is administered in combination or in alternation with Remdesivir to amplify the overall antiviral effect.

Stage 3, the final stage of the disease, is characterized by progressive disseminated intravascular coagulation (DIC), a condition in which small blood clots develop throughout the bloodstream. This stage also can include multi-organ failure (e.g. vasodilatory shock, myocarditis). It has also been observed that many patients respond to this severe stage of COVID-19 infection with a "cytokine storm." There does appear to be a bi-directional, synergistic relationship between DIC and cytokine storm. To combat DIC, patients are often administered an anti-coagulant agent, which may, for example, be an indirect thrombin inhibitor or a direct oral anticoagulant ("DOAC"). Non-limiting examples are low-molecular weight heparin, warfarin, the product bivalirudin sold under the trademark ANGIOMAX, the product rivaroxaban sold under the trademark XARELTO, the product dabigatran sold under the trademark PRADAXA, the product apixaban sold under the trademark ELIQUIS, or the product edoxaban sold under the trademark LIXIANA. In one embodiment, a compound of the present invention is administered in combination or in alternation with anticoagulant therapy. In some severe cases of clotting in COVID patients, TPA can be administered (tissue plasminogen activator).

It has been observed that high levels of the cytokine interleukin-6 (IL-6) are a precursor to respiratory failure and death in COVID-19 patients. To treat this surge of an immune response, which may constitute a cytokine storm, patients can be administered an IL-6-targeting monoclonal antibody, pharmaceutical inhibitor or protein degrader such as a bispecific compound that binds to IL-6 and also to a protein that mediates degradation. Examples of antibodies include tocilizumab, sarilumab, siltuximab, olokizumab and clazakizumab. In one embodiment, a compound of the present invention is administered in combination or in alternation with tocilizumab or sarilumab. Additional non-limiting examples of immunosuppressant drugs used to treat the overreacting immune system include Janus kinase inhibitors (the product tofacitinib 1 under the trademark XELJANZ; calcineurin inhibitors (the product cyclosporine d under the trademarks NEORAL, SANDIMMUNE and SANGCYA, the product tacrolimus sold under the trademarks ASTAGRAF XL. ENVARUS XR and PROGRAF; mTOR inhibitors (the product sirolimus sold under the trademark RAPAMUNE, the product everolimus sold under the trademarks AFINITOR and ZORTRESS; and, IMDH inhibitors (the product azathioprine sold under the trademarks AZASAN and IMURAN, the product leflunomide sold under the trademark ARAVA, the product mycophenolate sold under the trademarks CELLCEPT and MYFORTIC. Additional antibodies and biologics include the product abatacept sold under the trademark ORENCIA, the product adalimumab sold under the trademark HUMIRA, the product anakinra sold under the trademark KINERET, the product certolizumab sold under the name CIMZIA, the product etanercept sold under the trademark ENBREL, the product golimumab sold under the name SIMPONI, the product infliximab sold under the trademark REMICADE, the product ixekizumab sold under the trademark TALTZ, the product natalizumab sold under the trademark TYSABRI, the product rituximab d under the trademark RITUXAN, the product secukinumab sold under the trademark COSENTYX, the product tocilizumab sold under the trademark ACTEMRA, the product ustekinumab sold under the trademark STELARA, the product vedolizumab sold under the trademark ENTYVIO, the product basiliximab sold under the trademark SIMULECT, and the product daclizumab sold under the trademark ZINBRYTA.

IL-1 blocks the production of IL-6 and other proinflammatory cytokines. COVID patients are also sometimes treated with anti-IL-1 therapy to reduce a hyperinflammatory response, for example, an intravenous administration of anakinra. Anti-IL-1 therapy generally may be for example, a targeting monoclonal antibody, pharmaceutical inhibitor or protein degrader such as a bispecific compound that binds to IL-1 and also to a protein that mediates degradation.

Patients with COVID often develop viral pneumonia, which can lead to bacterial pneumonia. Patients with severe COVID-19 can also be affected by sepsis or "septic shock". Treatment for bacterial pneumonia secondary to COVID or for sepsis includes the administration of antibiotics, for example a macrolide antibiotic, including azithromycin, clarithromycin, erythromycin, or roxithromycin. Additional antibiotics include amoxicillin, doxycycline, cephalexin, ciprofloxacin, clindamycin, metronidazole, sulfamethoxazole, trimethoprim, amoxicillin, clavulanate, or levofloxacin. In one embodiment, thus a compound of the present invention, is administered in combination or in alternation with an antibiotic, for example, azithromycin. Some of these antibiotics such as azithromycin have independent anti-inflammatory properties. Such drugs may be used both as anti-inflammatory agents for COVID patients and have a treatment effect on secondary bacterial infections.

A unique challenge in treating patients infected with COVID-19 is the relatively long-term need for sedation if patients require mechanical ventilation which might last up to or greater than 5, 10 or even 14 days. For ongoing pain during this treatment, analgesics can be added sequentially, and for ongoing anxiety, sedatives can be added sequentially. Non-limiting examples of analgesics include acetaminophen, ketamine, and PRN opioids (hydromorphone, fentanyl, and morphine). Non-limiting examples of sedatives include melatonin, atypical antipsychotics with sedative-predominant properties (olanzapine, quetiapine), propofol or dexmedetomidine, haloperidol, and phenobarbital. In one embodiment, a compound of the present invention is administered in combination or in alternation with a pain reliever, such as acetaminophen, ketamine, hydromorphone, fentanyl, or morphine. In one embodiment, a compound of the present invention is administered in combination or in alternation with a sedative, such as melatonin, olanzapine, quetiapine, propofol, dexmedetomidine, haloperidol, or phenobarbital.

Investigational drugs for COVID-19 include chloroquine and hydroxychloroquine. In one embodiment, a compound of the present invention, is administered in combination or in alternation with chloroquine or hydroxychloroquine.

A protease inhibitor such as lopinavir or ritonavir, previously approved for HIV, may also be administered.

Additional drugs that may be used in the treatment of a COVID patient include, but are not limited to favipiravir, the product fingolimod sold under the trademark GILENYA, methylprednisolone, the product bevacizumab sold under the trademark AVASTIN, the product Actemra sold under the trademark TOCILIZUMAB, umifenovir, losartan and the monoclonal antibody combination of REGN3048 and REGN3051 or ribavirin. Any of these drugs or vaccines can be used in combination or alternation with an active compound provided herein to treat a viral infection susceptible to such.

In one embodiment, a compound of the present invention is used in an effective amount in combination with anti-coronavirus vaccine therapy, including but not limited to mRNA-1273 (Moderna, Inc.), AZD-1222 (AstraZeneca and University of Oxford), BNT162 (Pfizer and BioNTech), the product CoronaVac sold under the trademark SINOVAC, NVX-CoV 2372 (NovoVax), SCB-2019 (Sanofi and GSK), ZYCOV-D (Zydus Cadila), and COVAXIN (Bharat Biotech). In another embodiment, a compound of the present invention is used in an effective amount in combination with passive antibody therapy or convalescent plasma therapy.

In an embodiment, a compound of the present invention is used in an effective amount in combination with a 5-HT receptor antagonists, which can relieve certain symptoms that might be present in a patient infected with coronavirus, such as diarrhea.

SARS-CoV-2 is constantly mutating, which many increase virulence and transmission rates. Drug-resistant variants of viruses may emerge after prolonged treatment with an antiviral agent. Drug resistance may occur by mutation of a gene that encodes for an enzyme used in viral replication. The efficacy of a drug against an RNA virus infection in certain cases can be prolonged, augmented, or restored by administering the compound in combination or alternation with another, and perhaps even two or three other, antiviral compounds that induce a different mutation or act through a different pathway, from that of the principle drug.

The present invention has multiple aspects, illustrated by the following non-limiting examples. The following examples are given for the purpose of illustrating various embodiments of the invention and are not meant to limit the present invention in any fashion.

EXAMPLES

Example 1: Assessment of the Anti-Viral Activity of ABC294640 Against SARS-CoV-2 in Human Airway Epithelial Cells We designed an in vitro assessment in an organotypic air-liquid-interface (ALI) culture of human primary bronchial epithelial cells (HBEC; EpiAirway™, MatTek) to evaluate whether infection and spread of SARS-CoV-2 could be directly inhibited by opaganib. This human cell culture model system was selected because it contains a pseudostratified epithelial layer that morphologically and functionally resembles that of the human airway, consisting of ciliated and goblet (mucus producing) cells exposed to the air from the apical layer. These cells act as the first line of defense against invading viruses and serve as replication sites. Available evidence also suggests that human bronchial epithelial cells express the host factors targeted by opaganib (sphingosine kinase-2).

Test Compounds:

Opaganib-Test Compound

Description: Opaganib [3-(4-chlorophenyl)-adamantane-1-carboxylic acid (pyridin-4-ylmethyl) amide, hydrochloride salt] is an orally available inhibitor of the enzyme sphingosine kinase-2 (SK2). Solvent: DMSO Remdesivir (GS-5734)—Positive Anti-viral Control Description: Remdesivir is a nucleotide-analog anti-viral prodrug. It exhibits anti-viral activity against multiple variants of EBOV with EC50 value ranging in 0.06-0.14 μM in cell-based assays and broad-spectrum anti-viral activity in vitro against other pathogenic RNA viruses, including SARS-CoV. Solvent: DMSO 100 mg/mL (166.0 mM)

Bleomycin (sulfate)—Positive Cytotoxic Control

Description: Bleomycin is a chemotherapy agent commonly used for the treatment of Hodgkin's lymphoma and embryonal carcinomas. A broad spectrum of bleomycin-induced pulmonary toxicities have been well described as a complication of such therapy, the most common variant of which is bleomycin-induced pneumonitis (BIP) (Sleijfer et al., 2001). Bleomycin (BLM) is chosen as the best-studied micronucleus (MN) inducers in human lymphocytes with different mechanisms of genotoxicity. Solvent: DMSO 16.67 mg/mL (11.2 mM)

Methods:

Cell Culture-Differentiated Human Bronchial Epithelial Cells (HBEC)

Normal human bronchial epithelial (HBEC) cells were differentiated by MatTek Corporation (Ashland, Mass.) and arrived in kits with either 12- or 24-well inserts each. HBEC cells were grown on 6 mm^2 mesh disks in transwell inserts. Three days prior to shipment, the tissues were transferred into hydrocortisone-free medium. During transportation the tissues were stabilized on a sheet of agarose, which was removed upon receipt. One insert was estimated to consist of approximately $1.2\times10^6$ cells. Kits of cell inserts (EpiAirway™ AIR-100) originated from a single donor, #9831, a 23-year old, healthy, non-smoking, Caucasian male. The cells have unique properties in forming layers, the apical side of which is exposed only to air and that creates a mucin layer. Upon arrival, the cell transwell inserts were immediately transferred to individual wells of a 6-well plate according to manufacturer's instructions, and 1 mL of MatTek's proprietary culture medium (AIR-100-MM) was added to the basolateral side, whereas the apical side was exposed to a humidified 5% $CO_2$ environment. Cells were cultured at 37° C. for one day before the start of the experiment. After the 16-18 h equilibration period, the mucin layer, secreted from the apical side of the cells, was removed by washing with 400 μL pre-warmed TEER buffer. Culture medium was replenished following the wash step. A depiction of the culture inserts and EpiAirway tissue provided in FIG. 1.

Treatment with Test Compounds:

Test compounds were serially diluted from stock solution (containing DMSO) in Assay medium (AIR-ASY-100, MatTek) and placed at room temperature. Test compound dilutions are outlined below (final DMSO<0.5%). HBEC cultures were washed with phosphate-buffered saline (PBS) and incubated at 37° C. with remdesivir (2 μM), bleomycin sulfate (75.6 and 151 μg/ml) and opaganib (6 concentrations ranging from 0.05 to 11.25 μg/ml) diluted in assay medium (AIR-100-ASY, MatTek) for 1 h prior to infection. For control wells, assay medium with DMSO (final DMSO<0.5%; control) and virus only control (assay medium only) were added for the 1 h before infection. Compounds were added to each insert on the apical layer (0.15 mL) and basal layer (0.85 mL) in triplicate.

Viral Infection and Sample Processing:

After 1 hr incubation with compounds, the apical side of the cultures were washed and then infected with SARS-CoV-2 clinical isolate (2019-nCoV/USA-WA1/2020) at MOI=0.1 PFU/cell for 1 h at 37° C., in the presence of compound or assay control media. After 1 hr viral incubation, the virus was removed from the apical side, and cultures were washed one time with PBS to remove any unbound virus. The cultures were then incubated at 37° C. for 72 h with fresh compound. At 24 h and 48 h post-infection, the basolateral medium was replaced with 1 mL of fresh medium containing the respective compounds.

At 72 hours post-infection, tissues and media were collected for processing. The apical layer was washed with 0.4 mL of TEER buffer (PBS with $Mg^{2+}$ and $Ca^{2+}$) and collected for viral titer assessment via TCID50 (50% tissue culture infectious dose) assay. Eight-fold serial dilutions of apical layer supernatant sample concentrations were added to 96-well assay plates containing Vero E6 cells (20,000/well). The plates were incubated at 37° C., 5% $CO_2$ and 95% relative humidity. Following 3 days (72±4 h) incubation, the plates were stained with crystal violet to measure cytopathic effect (CPE). Virus titers were calculated using the method of Reed and Muench (Reed et al., 1938). The $TCID_{50}$ values were determined from triplicate samples.

To evaluate the health of HBEC cells after exposure to opaganib, control compounds, and viral infection, a lactate dehydrogenase (LDH) release assay was conducted. Medium from the basolateral layer of the tissue culture inserts was removed 72 hours post-infection and diluted in LDH Storage Buffer as per the manufacturer's instructions (Promega). Samples were further diluted with LDH Buffer and incubated with an equal volume of LDH Detection Reagent. Luminescence was recorded after 60 minutes incubation at room temperature. A no cell control was included as a negative control to determine culture medium background and bleomycin included as a positive cytotoxic control. Luminescence was reported, with background levels found within the acceptable luminescence range (range 1,000-10,000).

Additionally, the apical layer of the HBEC tissues were collected by adding Trizol LS (Invitrogen) to each culture insert and pipetting up and down several times to lyse and collect the cells and store at −80° C. for future RNA and protein expression analysis.

Results:

Opaganib, is Highly Active Against SARS-CoV-2 in HBEC Cultures

In this study, normal human bronchial epithelial cells (HBEC) were pretreated in triplicate with 6 different concentrations of opaganib (ranging from 11.25 to 0.05 µg/ml) both on the apical and basolateral side of each culture. Once pretreated, HBEC were exposed to SARS-CoV-2 (2019-nCoV/USA-WA1/2020) for 1 h, the apical layer was washed to remove unbound virus, and the culture then incubated for 3 days with compound. At 3 days post infection, the apical layer was washed and assessed for viral load by TCID50 assay. The basolateral media was collected and assessed for presence of lactate dehydrogenase (LDH), which is released from damaged cells serving as an indicator of cell death/viability.

Figure 2:
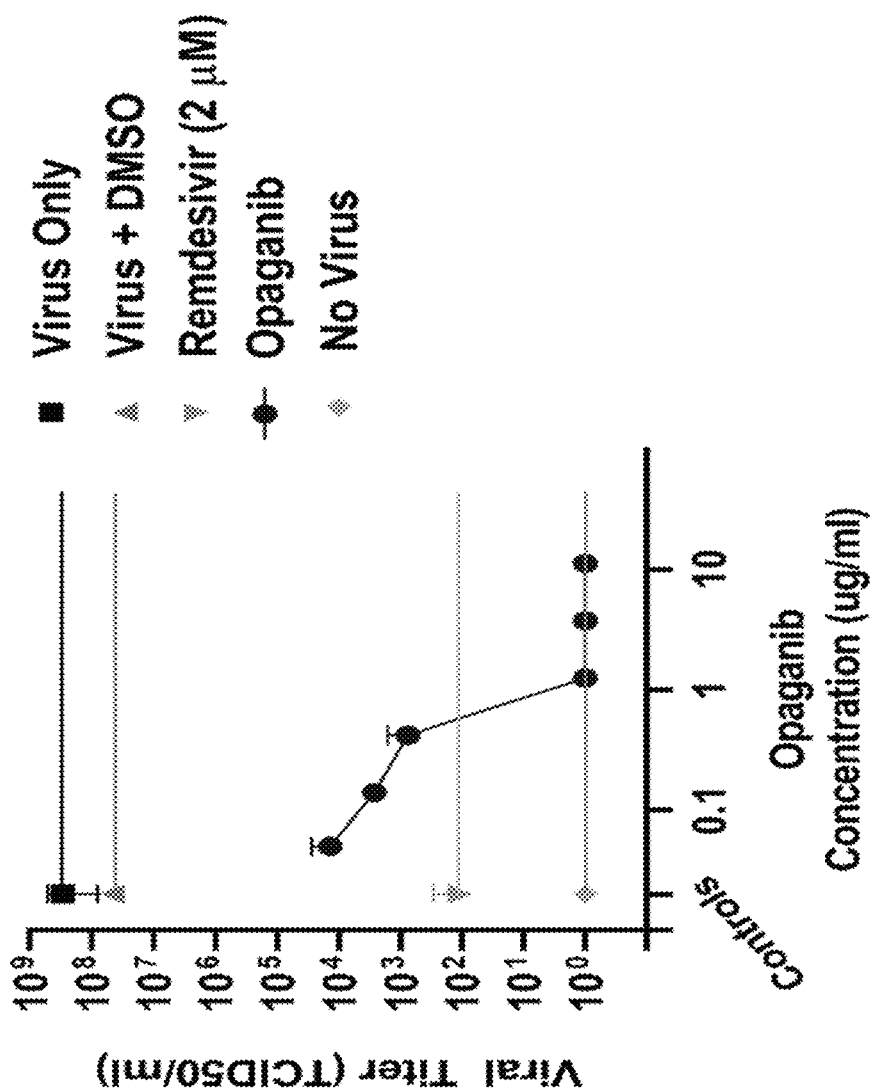
FIG. 2. is a graph showing that in opaganib-treated, SARS-CoV-2-infected HBEC cultures, after 3 days incubation, show a dose-dependent reduction in infectious virus production was observed at pharmacologically relevant concentrations.

Opaganib demonstrated potent anti-viral activity, with viral replication being inhibited in a dose-dependent manner without significant compromise to cell viability. In opaganib-treated, SARS-CoV-2-infected HBEC cultures, after 3 days incubation, a dose-dependent reduction in infectious virus production was observed with complete inhibition starting at opaganib 1 µg/ml (a pharmacologically relevant concentration). These results compare favorably with remdesivir, the positive control in the study. Cell viability, as assessed in the LDH release assay, To demonstrate the anti-viral activity of opaganib against SARS-CoV-2 in a human primary epithelial culture system, we performed anti-viral assays in HBEC cultures, which are grown on air-liquid interface and recapitulate the cellular complexity and physiology of the human conducting airway. In opaganib-treated, SARS-CoV-2-infected HBEC cultures, after 3 days incubation, a dose-dependent reduction in infectious virus production was observed with complete inhibition starting at opaganib 1 µg/ml (a pharmacologically relevant concentration) (FIG. 2). These results compare favorably with remdesivir, the positive control in the study.

Figure 3:
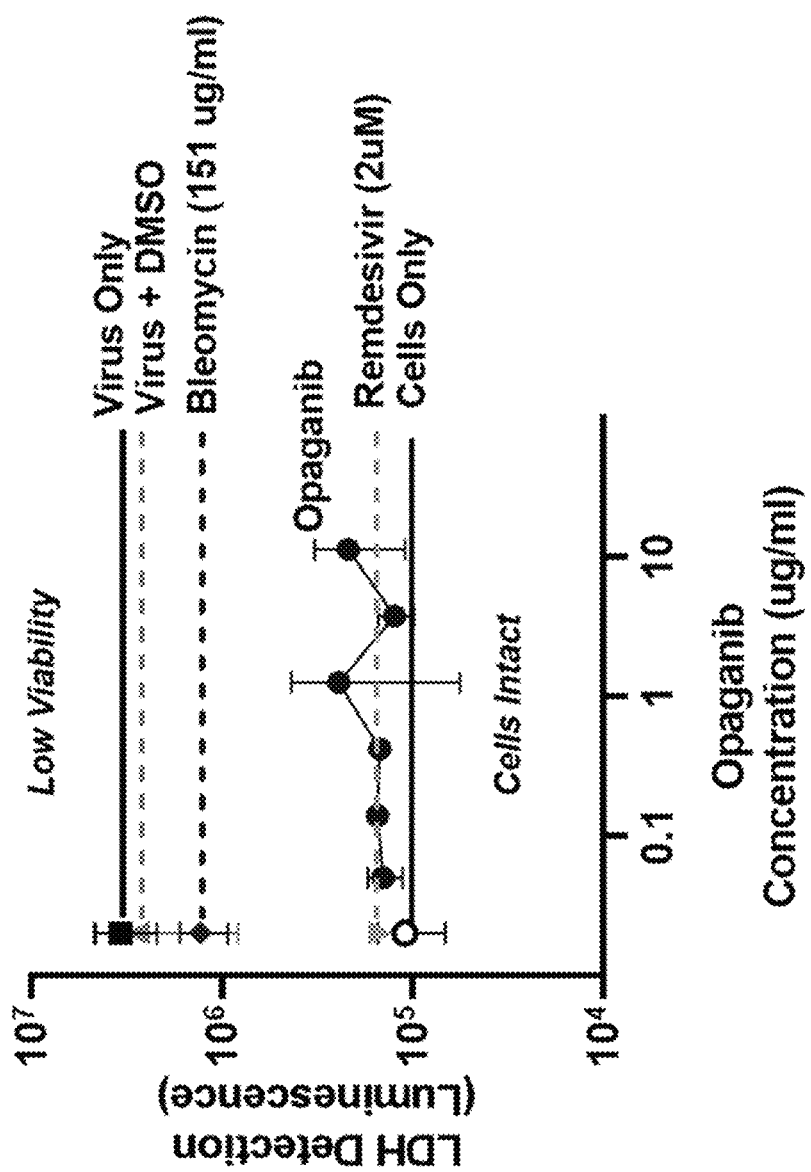
FIG. 3 is a graph showing opaganib-treated, SARS-CoV-2-infected HBEC cultures, after 3 days incubation, show limited cytotoxicity across the dose range where the potent anti-viral effects are seen.

Opaganib did not cause cytotoxicity in HBEC cultures across the concentration range where the potent anti-viral effects are seen (FIG. 3). Together, these data demonstrate that opaganib is potently anti-viral against SARS-CoV-2 in primary human lung cultures without compromising cell membrane integrity, a measure of cell viability and drug safety, further demonstrating opaganib's promising potential for treating patients with COVID-19.

At the concentration range tested, neither 50% inhibition nor 50% cytotoxicity were reached. At the lowest concentration tested, 0.05 µg/ml, greater than 90% inhibition of infectious virus production was reached. At highest concentration tested, 11.25 µg/ml, the cells remained viable throughout the experiment. When utilizing the high and low concentration range from this experiment to calculate the selectivity index (SI), the ratio that measures the window between cytotoxicity and antiviral activity by dividing the antiviral activity value (AVA) into the toxicity (TOX) value (AVA/TOX), the SI value is 225. The SI value is expected to be greater if a wider range of concentrations are tested.

Example 2: Assessment of In Vivo Efficacy of ABC294640 Against ARDS Induced Thrombosis This study assessed the efficacy of ABC294640 to reduce the incidence of adverse thromboembolic events in situ in acute respiratory distress syndrome (ARDS) conditions using a rat venous stasis model. This assay is designed to measure thrombotic risks following LPS-induced lung injury. LPS-induced lung injury is one of the most commonly used rodent models for ARDS and was described to mimic the neutrophilic inflammatory response observed in ARDS patients. The mechanism of LPS-induced ARDS is based on damage to endothelial cells and a systemic inflammatory response.

The venous stasis (Wessler) test in animals has been used extensively for over 40 years as a laboratory measure for in vivo hypercoagulability. It has proved invaluable for assessing the thrombogenicity of various blood products.

Test compound was administered by oral gavage 3 hours post-instillation and 24, 48 and 72 hours post-instillation, at a dose of 250 mg/kg. The appropriate amount of LPS from E. coli (O55:B5) was diluted in saline to obtain a final concentration of 400 µg/mL. This solution was given by intratracheal instillation (0.5 mL/kg). The vehicle was composed of PBS pH 7.4 f 0.1. ABC294640 was weighed and transferred in vehicle (PBS, 0.375%, pH 7.4) to obtain a final solution at 25 mg/mL. ABC294640 solution is stirred for 10 minutes at room temperature prior to dosing. This solution was given by oral gavage (250 mg/kg, 10 mL/kg).

Sprague-Dawley rats (male) weighing between 275 and 400 g were used for this study. Animals were randomly assigned to a treatment group by the Study Director. Food and water were given ad libitum. Observation for behavior and general health status were done until the sacrifice. The body weight was recorded before the instillation and 24, 48 and 72 hours post-instillation.

Arterial oxygen saturation ($SpO_2$) and heart rate was recorded with a mouse pulse oximeter collar probe installed on the conscious mouse (MouseOx Plus system, Starr Life Sciences) before instillation and 24, 48 and 72 hours post-instillation. Rats were also introduced into the plethysmograph chamber environment, same schedule as $SpO_2$. The functional respiratory parameters were assessed by the whole-body plethysmograph (VivoFlow, SCIREQ). The functional respiratory parameters analyzed included; the respiratory rate, the PenH (pulmonary congestion index) and the inspiratory/expiratory time measurements. A blood sample was also taken prior terminal procedure for complete blood count and cytokines level evaluation.

In this study, ARDS was induced by intratracheal instillation of LPS. Throughout the ARDS induction and development process, animal was dosed by oral gavage with vehicle or ABC294640 (3 h, 24 h, 48 and 72 hours post-instillation). Following 72 hours conscious measurements, rats were anesthetized and a venous stasis was performed on the inferior vena cava (4 hours post-gavage of 72 hour time point). The stasis was maintained for 30 minutes. The segment was then excised and its content scored. Subsequently, animal was euthanized by exsanguination.

After exsanguination, a tracheotomy was performed and the thoracic cavity opened to expose the lungs. The trachea was then connected to the cannula of a perfusion system. The left lung clamped while cold PBS 1×, Protease Inhibitor 1× solution was injected, by the trachea to perform a bronchoalveolar lavage fluid (BALF) on the right lobes of the lungs and was collected for further analysis. The total cells count with cells differential count and the total protein content was assessed in the BALF samples. An aliquot of the BALF was kept for the quantification of the chemokines/cytokine's levels in BALF.

The left lobe of the lungs was excised. The left lobe freshly harvested was weighed wet to determine the left lung weight and left lung index (left lung weight/body weight× 100). The lower part of the left lobe was used to determine the left lung wet/dry ratio, an indicator of pulmonary edema. The remaining part of the left lung was homogenized and aliquoted for the quantification of protein content.

Induction of LPS Lung Injury:
1. Prior LPS or saline instillation, the functional respiratory parameters of all rat was assessed by whole-body plethysmography and $SpO_2$ was evaluated on conscious rat with a collar probe pulse oximeter. Rat was first acclimatized to the plethysmograph chamber prior to the physiological assessment. The respiratory rate, the Penh and the inspiratory/expiratory time measurements was analyzed.
2. Rats were anaesthetized with 2.5% isoflurane USP (Abbot Laboratories, Montreal Canada) in oxygen. Rats were then intubated and LPS or saline delivered by intratracheal instillation.
3. Rats recovered from anesthesia and returned to their respective cage.
4. Three hours post instillation, the first dose of ABC294640 was administered by oral gavage (see Table 1 below).

TABLE 1

Experimental Progression/Steps for Rats

| | | | Gavage | | |
|---|---|---|---|---|---|
| Group | Instillation | Test compound | Composition | Dose (mg/kg) | Volume (mL/kg) |
| 1 | Saline | Vehicle | 0.9% NaCl | N/A | 10 |
| 2 | LPS | Vehicle | 0.9% NaCl | N/A | 10 |
| 3 | LPS | ABC294640 | 25 mg/mL | 250 | 10 |

5. Rats were evaluated periodically to ensure animal well-being (general behavior and daily body weight).
6. Animals were also dosed by oral gavage 24, 48 and 72 hours post-instillation.
7. $SpO_2$ and whole-body plethysmography were also evaluated 24, 48 and 72 hours post-instillation.
8. A blood sample was withdrawn from jugular vein prior venous stasis procedure for complete blood count and cytokines level measurements.
9. Four hours following the last dosing, rats were anaesthetized with 2.5% isoflurane USP (Abbot Laboratories, Montreal Canada) in oxygen. The procedure was performed on a homeothermic blanket to control body temperature.
10. The rat's inferior vena cava was exposed and two (2) loose sutures were placed 1 cm apart. Any collateral vessels of the isolated segment were ligated.
11. Stasis was maintained in situ for a period 30 minutes.
12. The venous stasis segment was removed, opened longitudinally, emptied on a filter paper and photographed. Any existing thrombi was removed and blotted on a filter paper. The thrombi was measured, weighed and scored on a scale from 0 to 4 (see Table 2).

TABLE 2

Quantitative Evaluation of Thrombogenicity

| Quantitative evaluation of thrombogenicity | Score |
|---|---|
| No clot | 0 |
| Few macroscopic strands of fibrin are barely visible | 0.5 |
| Few macroscopic strands of fibrin | 1.0 |
| One or several thrombi ≤1.5 mm | 1.5 |
| One thrombi ≥1.5 mm | 2.0 |
| Two or more thrombi ≥1.5 mm | 2.5 |
| One large thrombus ≥3 mm | 3.0 |
| Two or more large thrombi ≥3 mm | 3.5 |
| Single Thrombus forming the whole segment | 4.0 |

13. Following venous stasis, the animals were euthanized by exsanguination and bronchoalveolar lavage was collected from the right lung. To do so, the muscle over the trachea was dissected away prior to performing a tracheotomy. The thoracic cavity was opened to expose the lungs and the trachea was connected to the cannula of a perfusion system. The left lung was clamped while 15 mL (3×5 mL) of cold PBS 1×, Protease Inhibitor 1× solution was injected by the trachea to perform a bronchoalveolar lavage fluid (BALF) on the right lobe of the lungs. BALF was collected for further analysis. The total cells count with cells differential count was assessed in the BALF samples. An aliquot of the BALF was kept for quantification of the chemokines/cytokines levels in BALF.
14. The left lung was then harvested and weighed for left lung weight and left lung index calculation. Lung tissue edema was assessed using wet/dry ratio calculation. The lower part of the left lung was weighted alone (wet weight) and used to determine the lung wet/dry ratio. Following drying at 60° C. for at least 24 hours, it was reweighed (dry weight).

Each parameter (listed below) were compiled for each group and presented in bar graphs with appropriate statistical analysis.

1—Change in body weight
2—Saturation ($SpO_2$) and Heart Rate (bpm)
3—Respiratory parameters: Inspiratory/Expiratory Time
 Tidal and expired volume
 Respiratory Rate
 PenH
4—BALF total cell count with cells differential
5—BALF Cytokines/Chemokines Levels
6—Left Lung Weight and index
7—Lung wet/dry ratio
8—Lung total protein content in the lung homogenate LPS induces a significant increase in lung weight associated with the inflammation and a lethargic state. This increase is associated with a severe edema as indicated by an important increase of the W/D ratio. Lung weight gain was greater in the LPS-vehicle group compared to the LPS-vehicle group, at 4 hours post-gavage of 72 hour time point. ABC294640, administered at 250 mg/kg demonstrated a reduction of thrombosis—evidenced by a reduction in blood clot length, weight and total thrombus score.

Example 3: Pilot Study—Treatment of COVID-19 with Pneumonia with Opaganib

Patients diagnosed with COVID-19 infection who have developed pneumonia and do not require mechanical ventilation or who have been mechanically ventilated for no more than 24 hours were assessed om this hospitalized study.

Primary Objectives:
1) To evaluate the safety and tolerability of opaganib dosed at 500 mg Q12 hours in patients hospitalized with COVID-19 infection
To evaluate viral shedding on opaganib treatment
Secondary/Exploratory May Include One or More of:
1) To evaluate vital signs in patients hospitalized with COVID-19 infection on opaganib treatment
2) To evaluate clinical improvement in patients hospitalized with COVID-19 infection on opaganib treatment
3) To evaluate the need for mechanical ventilation on opaganib treatment, for patients not mechanically ventilated at baseline
4) To evaluate the improvement in hypoxia either via $SpO_2$/FiO2 or PaO2/FiO2 ratio, and SpO2 on room air. Return to room air or a specific SpO2 oxygen saturation on room air.

Assessment of on-treatment viral load changes, and changes in D-dimer, cardiac troponin, LDH and ferritin levels.

Study Design:
This study included one active treatment arm; open-label opaganib 500 mg Q12 hour twice daily, for all eligible patients hospitalized with COVID-19 pneumonia who either do not require mechanical ventilation, or have received mechanical ventilation for <24 hours. Patients entered a screening period of up to 1 week. Eligible patients entered the treatment period for up to 2 weeks. All participants were followed for 2 weeks after their last dose of study drug, at the end of the 2 week treatment period, or once they had 2 consecutive daily negative viral swabs for the COVID-19 virus or at after premature drug discontinuation prior to Day 14. The maximum duration of study participation was 35 days (7 weeks). Study participants received opaganib, 2×250 mg capsules (500 mg) Q12 hours, administered daily for up to a total of 14 days (2 weeks) or until 2 consecutive daily nasopharyngeal viral swabs were negative for COVID-19, whichever came first. Opaganib was administered with food (after a light to moderate meal) and followed by 240 mL (8 fluid ounces) of water. If the patient was only able to take opaganib through a naso-gastric tube, the contents of the capsule were suspended in 20 cc normal saline solution and pushed through the naso-gastric tube and flushed adequately with sterile water. If the patient was being tube-fed, opaganib was administered shortly after (approximately 15-30 minutes) a tube feeding.

Key Inclusion Criteria:
1. Adult male or female≥18 to ≤75 years of age, inclusive
2. Proven COVID-19 infection and pneumonia not requiring mechanical ventilation or mechanically ventilated for no more than 24 hours at time of informed consent
3. The patient, guardian or legally acceptable representative has signed a written IRB-approved informed consent.

Key Exclusion Criteria:
1. New York Heart Association Class III or IV, cardiac disease, myocardial infarction within the past 6 months, unstable arrhythmia, or evidence of ischemia on ECG
2. Any co-morbidity that may add risk to the treatment in the judgement of the investigator.
3. Pregnant (positive serum test) or nursing women
4. Unwillingness or inability to comply with procedures required in this protocol.
5. AST (SGOT) or ALT (SGPT)>2.5× upper limit of normal (ULN)
6. Bilirubin>1.5×ULN (except where bilirubin increase is due to Gilbert's Syndrome)
7. Serum creatinine>2.0×ULN
8. Absolute neutrophil count<1000 cells/mm$^3$
9. Platelet count<75,000/mm$^3$
10. Hemoglobin<8.0 g/dL
11. Currently taking warfarin, apixaban, argatroban or rivaroxaban
12. Current drug or alcohol abuse Study Assessments:
The following will be monitored daily (see Table 3):
 Review of concomitant medications
 Adverse Events
 Physical exam
 Vital signs (temperature, blood pressure, pulse rate, respiratory rate and oxygen saturation by pulse oximeter)
 Clinical symptoms (cough, dyspnea, nausea, vomiting, diarrhea)
 Nasopharyngeal viral swab
 Serum chemistry
 CBC with differential
 Chest X-ray
 Urinalysis

TABLE 3

Schedule of Assessments; other possible assessments not mentioned below include collecting blood and stool samples and determining. SARS-CoV-2 RNA levels using a quantitative RT-PCR assay. Daily assessments of viral load as long as subjects continue to shed viral RNA.

| Assessments | Screening Days -7 to -1 | Random-ization Day 0 | Daily On-Treatment Assessments Days 1-14 inclusive[1] |
|---|---|---|---|
| ICF signed | X | | |
| Inclusion/exclusion criteria | X | | |
| Demographics; medical and surgical history | X | | |
| Review concomitant medication(s) | X | X | X |
| Review of systems | X | X | |
| Physical examination | X | X | X |
| Vital signs[2] | X | X | X |
| Clinical symptom evaluation[3] | | | |
| Weight | X | | |
| Nasopharyngeal viral swab and/or oropharyngeal swab | X | X | X |
| 12-lead ECG | X | | |
| Chest X-ray | X | X | X |
| Serum chemistry | X | X | X |
| Hematology (CBC) | X | X | X |
| Urinalysis | X | X | X |
| Serum pregnancy test[4] | X | | |

[1] daily assessments to Day 14 or earlier, if 2 daily consecutive negative viral swabs for SARS-CoV-2
[2] assess temperature, blood pressure, pulse rate, respiratory rate and oxygen saturation by pulse oximeter
[3] assess cough, dyspnea, nausea, vomiting, diarrhea
[4] women of childbearing potential; serum pregnancy test must be negative within 3 days prior to randomization Dosage Forms and Modes of Administration:

Opaganib was supplied as Capsules 250 mg, containing 250 mg opaganib along with excipients in white opaque hard gelatin capsules.

Opaganib was administered orally (or via naso-gastric tube where appropriate) as two capsules (500 mg) every 12 hours for up to 2 weeks. Each dose is administered with food or 15-30 minutes after tube-feeding, where appropriate.

Study Endpoints:
Primary Safety Endpoints:
1) Adverse events, laboratory tests, physical examination and vital signs
2) The percentage of patients with 2 negative consecutive daily nasopharyngeal viral swabs by Day 14 on opaganib treatment Secondary/Exploratory Endpoints:
1) The percentage of patients demonstrating vital sign improvement (based on improvements in one or more of the following: temperature, heart rate, respiratory rate, oxygen saturation)
2) The percentage of patients demonstrating clinical improvement (based on improvements in one or more of the following symptoms: cough, dyspnea, nausea, vomiting, diarrhea)

The percentage of patients, who were not mechanically ventilated at baseline who do not require mechanical ventilation by the end of the 2-week off-study-drug follow-up Results:
Results have been obtained from seven patients approved for compassionate use. These patients had moderate to severe COVID-19-related pneumonia with hypoxia on supplemental oxygen. The patients were given opaganib plus standard-of-care, including hydroxychloroquine (HCQ) as background therapy in six of the seven patients.

As can be seen from Table 4, with the exception of patient #7 who had only 1 day of treatment due to diarrhea that may or may not be related to opaganib (the patient was also given HCQ and Azithromycin), all 6 moderate to-severe patients improved significantly, with 5 patients back to breathing room air and 3 patients discharged from hospital.

All six patients have shown reduction in C-Reactive Protein (CRP), all six patients also demonstrated measurable clinical improvement, including reduced supplemental oxygenation and higher lymphocyte counts.

All patients started for first 3 days at 250 mg opaganib Q12 hours and then increased to 500 mg opaganib Q12 hours.

Despite being in only six patients, these preliminary findings show clinical improvement in the first COVID-19 patients treated with opaganib, and provide preliminary support for the tolerability of opaganib use in COVID-19 patients.

TABLE 4

Results from Study

| Patient (days on opaganib treatment) | Clinical Assessment | Laboratory | Baseline | Most recent (date) |
|---|---|---|---|---|
| Patient 1 (14 d) | Started as severe on maximal OptiFlow 3 Apr. 2020; RA by 16/4. As of 22/4, one negative viral swab | Lymphocytes $10^3/mm^3$ | 1.6 | 2.8 (17 Apr. 2020) |
| | | CRPmg/L | 15.1 | 1 (17 Apr. 2020) |
| Patient 2 (14 d) | Started as severe+, planning for intubation 7 Apr. 2020; RA by 20 Apr. 4 2020, D/C on 22 Apr. 2020 | Lymphocytes $10^3/mm^3$ | 1.1 | 2.1 (17 Apr. 2020) |
| | | CRP mg/L | 14.2 | 4.8 (17 Apr. 2020) |
| Patient 3 (7 d) | Moderate-severe, on OptiFlow 13 Apr. 2020; RA by 17 Apr. 2020, D/C on 19 Apr. 2020 | Lymphocytes $10^3/mm^3$ | 0.9 | 1.2 (17 Apr. 2020) |
| | | CRP mg/L | 10.7 | 1.7 (17 Apr. 2020) |
| Patient 4 (11 d) | Started severe+ 70% OptiFlow on 13 Apr. 2020; RA on 22 Apr. 2020 | Lymphocytes $10^3/mm^3$ | 1.2 | 1 (22 Apr. 2020) |
| | | CRP mg/L | 24.8 | 17.4 (22 Apr. 2020) |
| Patient 5 (2 d) | Started moderate on 13 Apr. 2020, nasal cannula. Dramatic improvement after one day on opaganib; D/C on 14 Apr. 2020 on RA | Lymphocytes $10^3/mm^3$ | 1.1 | * |
| | | CRP mg/L | 11 | * |

TABLE 4-continued

Results from Study

| Patient (days on opaganib treatment) | Clinical Assessment | Laboratory | Baseline | Most recent (date) |
|---|---|---|---|---|
| Patient 6 (5 d) | Started severe, high OptiFlow on 19 Apr. 2020. No HCQ due to stroke, pacemaker and prolonged QTc at baseline; down to nasal cannulas on 24 Apr. 2020 | Lymphocytes $10^3$/mm$^3$ | 1.35 | 1.96 (24 Apr. 2020) |
| | | CRP mg/L | 12.2 | 6.8 (24 Apr. 2020) |
| Patient 7 (1 d treatment discontinued) Started severe on high OptiFlow on 19 Apr. 2020; on HCQ and azithromycin <24 hours at the time treatment with opaganib started. Diarrhea the next day, all 3 meds were stopped, followed by worsening SOB, on 75% OptiFlow. On steroids only as of 24 Apr. 2020 | | | | |

* Improved one day after initiation of therapy, discharged on room air without repeat blood work.
RA - room air, D/C - discharged, SOB - shortness of breath Five patients were included in the analysis, and for comparison purposes, we used a control group with same-sex, same-severity patients (baseline characteristics). Univariate comparisons between the groups were performed with chi-square test for categorical variables and t-test or MannWhitney U-test for continuous variables, as appropriate. Time variables were compared with Cox proportional hazard regression, adjusted for age and background illnesses. CRP and lymphocyte changes were compared utilizing a repeated measures general linear model with a Bonferroni correction for multiple comparison.

Patients treated with opaganib had significantly faster increase in lymphocyte count. All other clinical outcomes had a non-statistically significant trend in favor of the treatment group: median time to weaning from high-flow nasal cannula (HFNC) was 10 and 15 days in cases vs. controls (HR=0.3, 95% CI: 0.07-1.7, p=0.2), time to ambient air was 13 vs 14.5 days (HR=0.4, 95% CI: 0.15-1.5), none of the cases required mechanical ventilation compared with 33% of controls. In this small cohort of severe COVID-19 patients, opaganib was safe and well tolerated with improvement in both clinical and laboratory parameters in all treated patients. The efficacy of opaganib for COVID-19 infection should be further tested in randomized placebo-controlled trials.

Example 4: Randomized, Double-Blind, Placebo-Controlled Phase 2a Study of Opaganib in COVID-19 Pneumonia Primary Objective:

To evaluate the total oxygen requirement (area under the curve) using daily supplemental oxygen flow (L/min) over 14 days (Day 1 to Day 14)

Secondary Objectives:
1) To evaluate the time to 50% reduction from baseline in supplemental oxygen based on oxygen flow in L/min
2) To evaluate the proportion of patients no longer requiring supplemental oxygen for at least 24 hours by Day 14
3) To evaluate the proportion of afebrile patients at Day 14
4) To evaluate the time to negative swabs for SARS-CoV-2 by PCR
5) To evaluate the proportion of patients with negative swabs for SARS-CoV-2 by PCR at Day 14
6) To evaluate the need for intubation and mechanical ventilation by Day 14
7) To evaluate the time to mechanical ventilation
8) To evaluate the proportion of patients, with at least one measurement of fever at baseline (defined as temperature>38.0 C [100.4 F]), who are afebrile (defined as temperature<37.2 C [99 F]) at Day 14
9) To evaluate mortality 30 days post-baseline Exploratory Objectives:

To assess the change in systemic markers of inflammation (D-dimer, cardiac troponin, C-reactive protein [CRP], lactate dehydrogenase [LDH] and ferritin)

Safety Objectives:

To assess the safety and tolerability of opaganib administered orally at 500 mg Q 12 hours, for up to 14 days, in patients with COVID-19 pneumonia Study Population:

The study population will consist of patients diagnosed with COVID-19 infection who have developed pneumonia defined as radiographic opacities on chest X-ray and require supplemental oxygen. The patients must be hospitalized at least during screening and at baseline (Day 1).

Study Design and Description:

This was a phase 2a, proof of concept, multi-center randomized double-blind, parallel arm, placebo-controlled study. After informed consent was obtained, patients entered a screening phase for no more than 3 days, to determine eligibility. 42 eligible patients were randomized to receive either opaganib added to standard of care, or matching placebo added to standard of care, in a randomization ratio of 1:1. Treatment assignments remained blinded to the patient, investigator and hospital staff, as well as the sponsor. As there was no consensus for a definitive treatment specifically targeting the SARS-CoV-2 virus causing COVID-19 (Wilson, 2020), standard of care referred to regional, institutional or physician directed therapies, that were implemented during the COVID-19 pandemic.

Study participants received either opaganib 2×250 mg capsules (500 mg) every 12 hours, or matching placebo, in addition to standard of care (pharmacological and/or supportive). Study drug was to be administered every day for 14 days (Day 1 to Day 14), unless the patient had been discharged from the hospital without requiring supplemental oxygen, in which case study drug would only be administered to Day 10.

All participants were followed up for 4 weeks after their last dose of study drug, which may have occurred at the end of the 2-week double-blind treatment phase or after premature study drug discontinuation, based upon patient or physician determination. The maximum duration of study participation was up to 45 days (including up to 3 days screening; 2 weeks DB treatment phase and 4-weeks off-study drug follow-up)

Stratification:
Patients were stratified based on a minimization algorithm taking the following three parameters into account: age at screening, ≥70 years of age, (yes or no); HbA1c at screening, ≥6.5, (yes or no); oxygen requirement at baseline, requiring non-invasive positive pressure ventilation (e.g. via BIPAP, CPAP), (yes or no).

Eligibility Criteria:

Inclusion:
1. Adult male or female≥18 to ≤80 years of age
2. Proven COVID-19 infection per RT-PCR assay of a pharyngeal sample (nasopharyngeal or oropharyngeal) AND pneumonia defined as radiographic opacities on chest X-ray
3. The patient requires supplemental oxygen at baseline
4. The patient, guardian or legal representative has signed a written IRB-approved informed consent Exclusion:
1. Any co-morbidity that may add risk to the treatment in the judgement of the investigator.
2. Requiring intubation and mechanical ventilation
3. Oxygen saturation≥95% on room air
4. Any preexisting respiratory condition that requires intermittent or continuous ambulatory oxygen prior to hospitalization
5. Patient is, in the investigator's clinical judgement, unlikely to survive >72 hours
6. Pregnant (positive serum test within 3 days prior to randomization) or nursing women
7. Unwillingness or inability to comply with procedures required in this protocol.
8. Corrected QT (QTc) interval on electrocardiogram (ECG) >470 ms for females or >450 ms for males, calculated using Friedericia's formula (QTcF)
9. AST (SGOT) or ALT (SGPT) >2.5× upper limit of normal (ULN)
10. Bilirubin>1.5×ULN (except where bilirubin increase is due to Gilbert's Syndrome)
11. Serum creatinine>2.0×ULN
12. Absolute neutrophil count<1000 cells/mm$^3$
13. Platelet count<75,000/mm$^3$
14. Hemoglobin<8.0 g/dL
15. Currently taking medications that are sensitive CYP3A4, CYP2C9 or CYP2C19 substrates and have a narrow therapeutic index
16. Currently taking medications that are strong inducers or inhibitors of CYP2D6 and CYP3A4
17. Currently taking warfarin, apixaban, argatroban or rivaroxaban
18. Current drug or alcohol abuse
19. Currently participating in a clinical study assessing pharmacological treatments, including anti-viral studies Number of Subjects:
A total of 49 patients were screened in the study, of which 42 patients were randomized (23 to opaganib, 19 to placebo) while 7 were screen failures. Two patients were randomized in each group but not treated. 19 opaganib patients and 16 placebo patients completed treatment (Day 14). 3 opaganib patients and 2 placebo patients discontinued the treatment prematurely. Two patients in the opaganib arm experienced adverse events such that study drug was terminated, while one placebo patient was terminated due to an adverse event.

Screening/Baseline Assessments:
  Signed informed consent
  Eligibility determination
  Complete medical history (including onset of COVID-19 symptoms)
  Concomitant medication assessment
  Baseline review of systems
  Physical examination
  Vital signs (temperature, blood pressure, pulse rate, respiratory rate and oxygen saturation by pulse oximeter)
  Weight if the patient is ambulatory
  Oxygen requirement (L/min)
  12-lead electrocardiogram
  Chest Xray
  Nasopharyngeal or oropharyngeal swab for SARS-CoV-2 PCR test
  Serum chemistry
  CRP, D-Dimer, LDH, ferritin, cardiac troponin
  HbA1c
  CBC with differential
  Urinalysis
  Serum pregnancy test (for women of childbearing potential) within 3 days prior to treatment Study Assessments:
The following were monitored and documented daily as part of the standard of care:
  Concomitant medications
  Adverse Events
  Interim Physical exam
  Vital signs (temperature, blood pressure, pulse rate, respiratory rate and oxygen saturation by pulse oximeter)
  Oxygen requirement (L/min)

The following will be monitored less frequently as part of standard of care and wherever possible:
  For patients on concomitant hydroxychloroquine, a 12-lead electrocardiogram (if allowed by hospital treatment guidelines under COVID-19) approximately 3 hours after the first study drug administration on Day 1, anytime on Days 2 and 4, and again at end-of-treatment (either Day 10, 14 or at premature study drug discontinuation). If patients are on monitors (including telemetry or Holter monitors), investigators are encouraged to collect QT interval data
  Nasopharyngeal or oropharyngeal viral swab for SARS-CoV-2 PCR test every 1-3 days
  Serum chemistry once weekly
  Serum CRP, D-Dimer, LDH, ferritin, cardiac troponin once weekly
  CBC with differential once weekly
  Chest X-ray as per physician decision Study Endpoints:

Primary
The total oxygen requirement (area under the curve) using the daily supplemental oxygen flow (L/min) over 14 days (Day 1 to Day 14)

Secondary
1) Time to 50% reduction from baseline in supplemental oxygen based on oxygen flow in L/min
2) The percentage of patients no longer receiving supplemental oxygen for at least 24 hours by Day 14
3) The time to two consecutive negative swabs for SARS-CoV-2 by PCR, at least 24 hours apart
4) The percentage of patients with at least two consecutive negative swabs, followed by continued negative swabs, for SARS-CoV-2 by PCR at Day 14
5) The percentage of patients requiring intubation and mechanical ventilation by the end of the 2-week off-study-drug follow-up
6) The time to intubation and mechanical ventilation 7) The percentage of patients with at least one measurement of fever at baseline (defined as temperature>38.0 C [100.4 F]), who are afebrile (defined as temperature<37.2 C [99 F]) at Day 14
8) Mortality due to any cause at Day 30

Exploratory
1) The mean change in systemic markers of inflammation (D-dimer, cardiac troponin, C-reactive protein [CRP], procalcitonin [PCT], lactate dehydrogenase [LDH] and ferritin) from baseline at Day 14

Safety
1) Incidence rates of all treatment-emergent AEs (TEAEs) and SAEs
2) Evaluation of vital signs
3) Evaluation of laboratory parameters (chemistry and hematology)
4) Evaluation of electrocardiograms (ECG)

Statistical Methods:

The primary efficacy objective of the study was to evaluate the effect of Opaganib on total supplemental oxygen requirement (area under the curve) using daily oxygen flow (L/min) measurements for 14 days (Day 1 to Day 14). The primary efficacy endpoint calculated for each patient the area under the curve of the supplemental oxygen requirement through day 14, using the trapezoidal rule after subtracting the baseline oxygen requirement at each day. Days where no supplementary oxygen was needed, were recorded as 0. If several values of oxygen requirement (L/min) are recorded in a certain day, for the primary analysis the highest of these values were taken. In the primary analysis, for patients who die before Day 14, or require intubation and mechanical ventilation, missing daily values were assigned the maximal supplemental oxygen flow requirement of 8 L/min. For patients discharged from hospital on supplemental oxygen prior to Day 14, if no values were collected by the site after discharge, the oxygen requirement (L/min) on the day of discharge were to be assigned thereafter for each day to Day 14.

The primary analysis was based on the modified Intent to treat population (mITT), which consist of all patients that were randomized and treated with at least one dose of study drug (the population included a total of 40 subjects, 22 in opaganib and 18 in placebo group), Descriptive statistics of the baseline-adjusted AUC are presented by group along with 95% confidence interval for each group and for the difference in means between the groups. Supplemental oxygen requirement up to Day 14 was collected even if a patient discontinued treatment prior to Day 14 but continued in the study to Day 14. Further, it was assumed that loss to follow up such that vital status up to Day 14 were missing is unlikely. Therefore, the primary analysis assumed that in case that all supplemental oxygen values are missing after treatment discontinuation, the last value is carried forward—until Day 14, or death, if occurred before. A sensitivity analysis to the above missing data handling approach was performed using an AUC summary statistics approach, in which groups AUC is calculated from the estimated parameters of a Repeated-Measures model.

Within the mITT cohort, two subjects withdrew their consent due to grade 1 gastrointestinal AEs. In addition, one subject did not require any supplemental oxygen at baseline prior to initiating treatment and was removed from several analyses as mandated in the statistical analysis plan (SAP). Thus, the post-hoc activity analysis population ("mITT sensitivity") excluded these three patients from the analysis and included 37 subjects, 19 in opaganib and 18 in placebo. The results for both the mITT population (which included these 3 subjects) and the mITT sensitivity population showed similar trends of activity.

Results:

Top-line results from the study found opaganib to be safe, with no material safety differences between the opaganib and placebo treatment arms. Overall, fewer patients suffered from serious adverse events (SAEs) in the opaganib treatment arm than in the placebo arm. In this small sample size, there were few events of intubation or fatality and these were balanced between the two arms.

Figure 4:
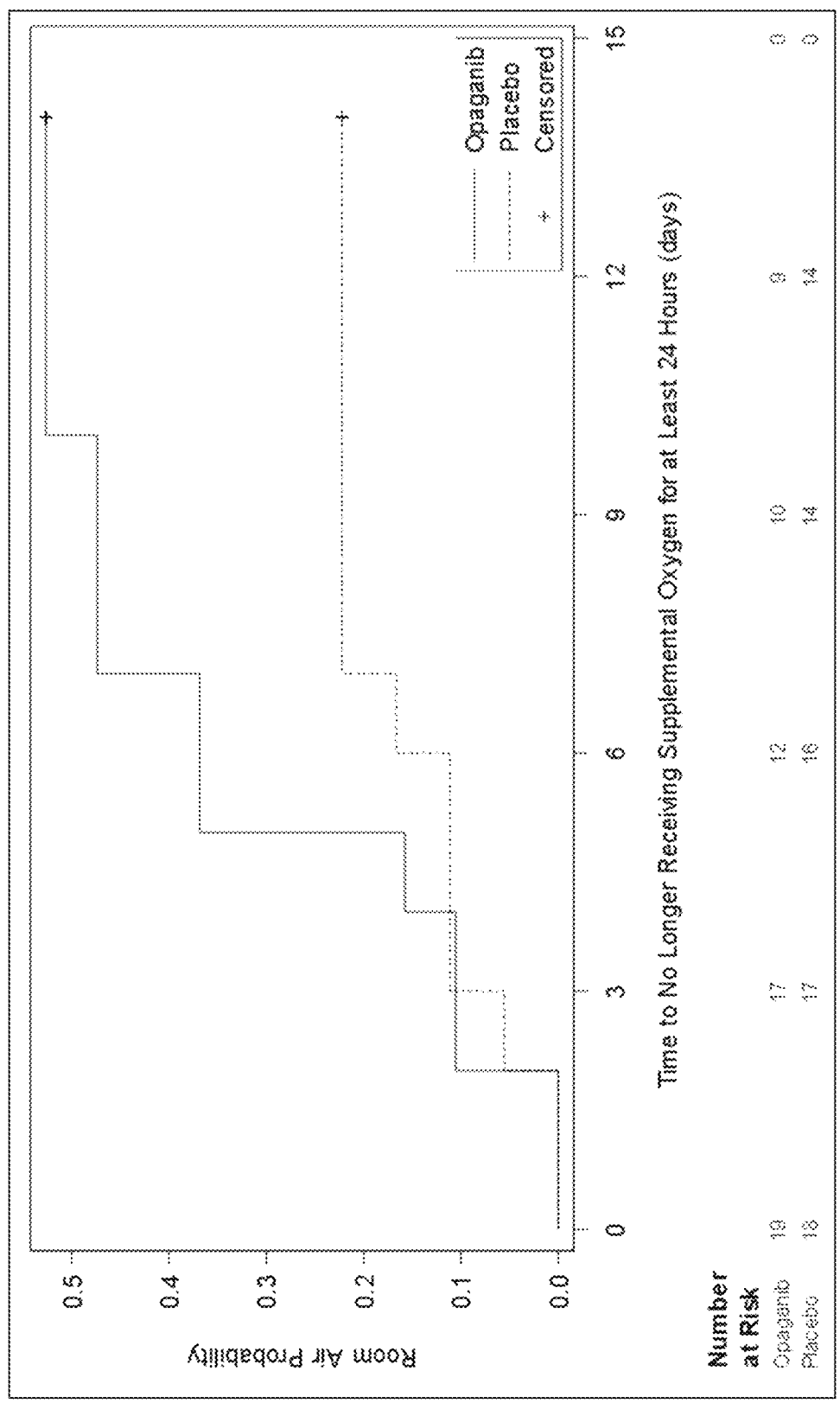
FIG. 4 shows a Kaplan-Meier curve of time to no longer receiving supplemental oxygen for at least 24 hours (mITT sensitivity) post statistical analysis from the randomized, double-blind, placebo-controlled Phase 2a study of opaganib in COVID-19 pneumonia described in Example 4.

The opaganib-treated arm demonstrated a consistent trend of greater improvement in reducing oxygen requirement by end of treatment on Day 14 across key primary and secondary efficacy outcomes, correlating with clinical improvement as defined by the World Health Organization (WHO) ordinal scale:

A greater improvement in the proportion of patients reaching room air and no longer requiring oxygen support by Day 14 vs. the control arm (52.6% vs. 22.2%). FIG. 4 shows a Kaplan-Meier curve of time to no longer receiving supplemental oxygen for at least 24 hours (mITT sensitivity).

Figure 5:
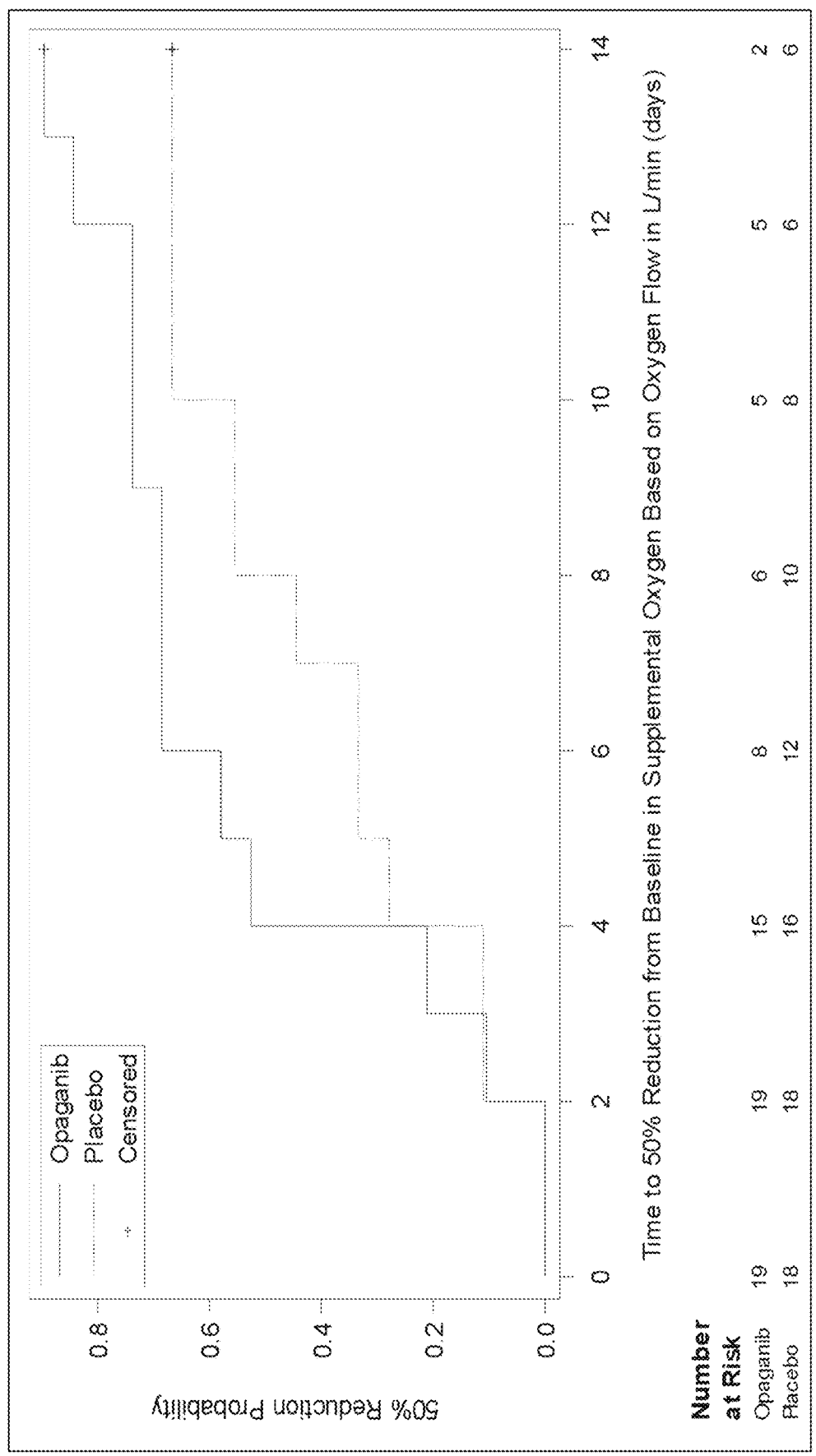
FIG. 5 shows a Kaplan-Meier curve of time cumulative incidence for time to 50% reduction from baseline in supplemental oxygen based on oxygen flow in L/min (mITT sensitivity) post statistical analysis from the randomized, double-blind, placebo-controlled Phase 2a study of opaganib in COVID-19 pneumonia described in Example 4.

A greater improvement in the proportion of patients with 50% reduction in supplemental oxygen by day 14 vs. the control arm (89.5% vs. 66.7%). FIG. 5 shows a Kaplan-Meier curve of time cumulative incidence for time to 50% reduction from baseline in supplemental oxygen based on oxygen flow in L/min (mITT sensitivity).

A higher proportion of patients discharged by Day 14 vs. the control arm (73.7% vs. 55.6%).

Figure 6:
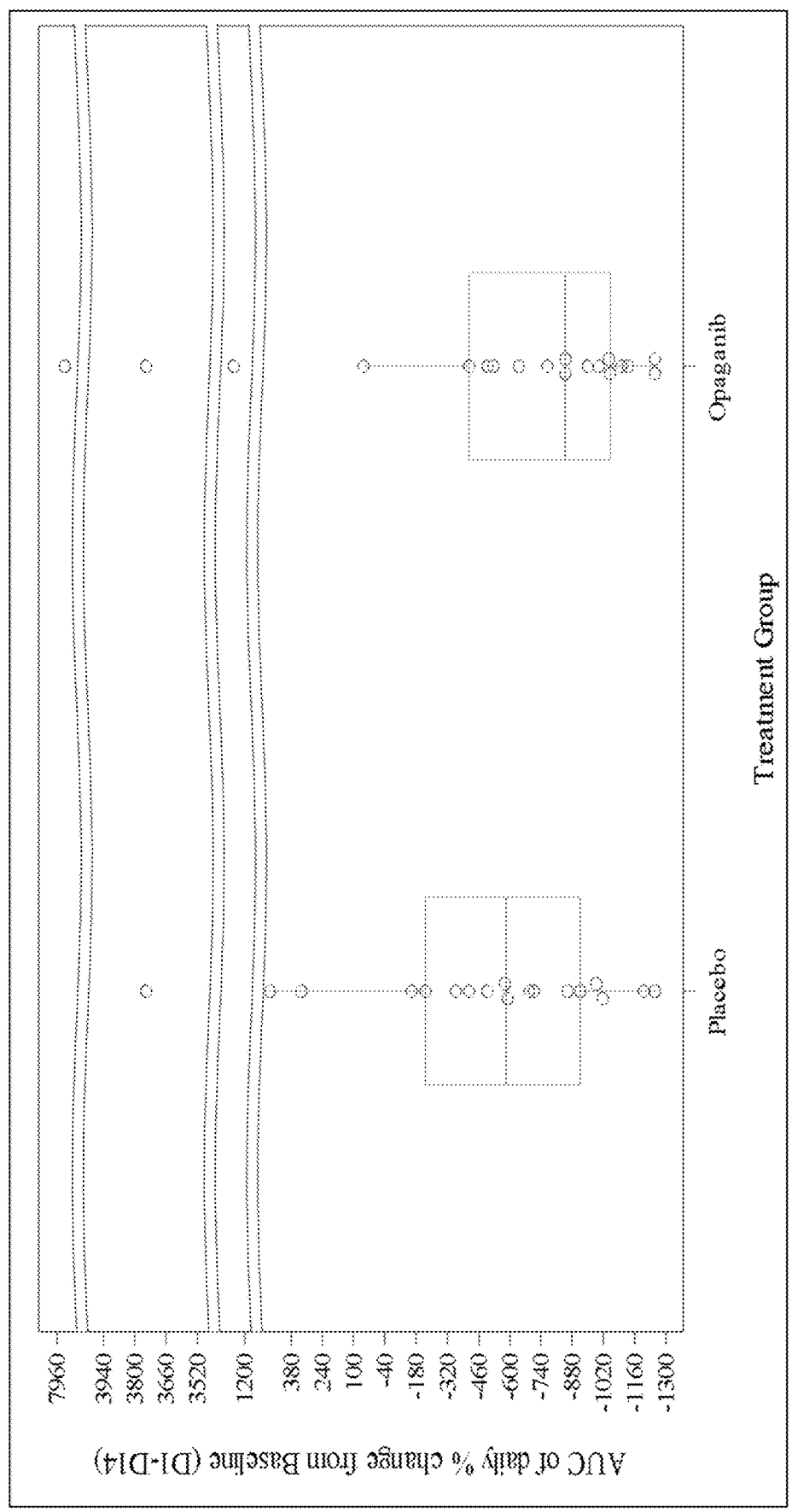
FIG. 6 shows a dot plot of total supplemental oxygen requirement (area under the curve) for percent change from baseline using daily oxygen flow (L/min) measurements for 14 days (day 1 to day 14) post statistical analysis from the randomized, double-blind, placebo-controlled Phase 2a study of opaganib in COVID-19 pneumonia described in Example 4.

Greater reduction from baseline of the medial total oxygen requirement (AUC) over 14 days (68.0% vs. 46.7%). FIG. 6 shows a dot plot of total supplemental oxygen requirement (area under the curve) for percent change from baseline using daily oxygen flow (L/min) measurements for 14 days (day 1 to day 14).

Example 5: Randomized, Double-Blind, Placebo-Controlled International Phase 2/3 Study—Opaganib in COVID-19 Pneumonia Primary Objective:
To evaluate the proportion of patients requiring intubation and mechanical ventilation by Day 14. The proportion of patients reaching room air by Day 14.

Secondary Objectives:
1) To evaluate change on the WHO Ordinal Scale for Clinical Improvement
2) To evaluate the time to intubation and mechanical ventilation
3) To evaluate the time to low oxygen flow via nasal cannula e.g. from high oxygen flow via nasal cannula or CPAP, if high oxygen flow is not an available option
4) To evaluate the proportion of patients no longer requiring supplemental oxygen for at least 24 hours by Day 14
5) To evaluate the total oxygen requirement (area under the curve) using daily supplemental oxygen flow (l/min) over 14 days (Day 1 to Day 14)
6) To evaluate the time to two consecutive negative swabs for SARS-CoV-2 by PCR
7) To evaluate the proportion of patients with two consecutive negative swabs for SARS-CoV-2 by PCR at Day 14
8) To evaluate the proportion of patients, with at least one measurement of fever at baseline (defined as temperature>38.0 C [100.4 F]), who are afebrile (defined as temperature<37.2 C [99 F]) at Day 14
9) To evaluate mortality 30 days post-baseline Explorative Objectives:

To assess the change in systemic markers of inflammation (D-dimer, cardiac troponin, C-reactive protein [CRP], lactate dehydrogenase [LDH] and ferritin) over the treatment period of 14 days.

Safety Objectives:

To assess the safety and tolerability of opaganib administered orally at 500 mg Q 12 hours, for up to 14 days, in patients with severe COVID-19 pneumonia.

Study Population:

The study population consisted of patients diagnosed with COVID-19 infection that was defined as severe based on eligibility criteria to align with current region-specific diagnostic guidance. Specifically, patients had at minimum pneumonia secondary to SARS-CoV-2, radiographic evidence of pneumonia on chest X-ray or CT scan, and required supplemental oxygen by high flow oxygen via nasal cannula, face mask or CPAP, if high oxygen flow was not an available option. Patients were hospitalized at least during screening and at Baseline (Day 1).

Study Design and Description:

This was a phase 2/3 multi-center randomized, double-blind, parallel arm, placebo—controlled study with an adaptive design that utilized a futility assessment. The study was conducted in 40 sites in 8 countries, including Europe, Israel, Latin America (was approved also in US and UK).

After informed consent was obtained, patients entered a screening phase (no more than 3 days), to determine eligibility. 475 patients were randomized and received either opaganib added to standard of care, or matching placebo added to standard of care, in a randomization ratio of 1:1. Treatment assignments remained blinded to the patient, investigator and hospital staff, as well as the sponsor. As the approval and/or guidance for treating COVID-19 was evolving, for this protocol, standard of care was defined by the recommended schemes of treatment according to the severity of the disease based on local diagnostic and guideline documents such as the Temporary Methodic Recommendations: Prophylactic, Diagnostics and Treatment of New Corona Virus Infection (COVID-19); the EU Commission, the European Medicines Agency (EMA), the Heads of Medicines Agency (HMA) and FDA, and as updated to the most current version of the recommendations.

Study participants received either opaganib 2×250 mg capsules (500 mg) every 12 hours, or matching placebo, in addition to standard of care (pharmacological as defined above and/or supportive) at any given institution. Study drug was administered every day for 14 days (Day 1 to Day 14). All participants were followed up for 28 days after their last dose of study drug, which occurred at Day 14 or after premature study drug discontinuation, based upon patient or physician determination.

Randomization Strategy:

As the treatments in the recommended schemes of treatment according to the severity of the disease differed, based on local diagnostic and guideline documents such as the Temporary Methodic Recommendations: Prophylactic, Diagnostics and Treatment of New Corona Virus Infection (COVID-19); the EU Commission, the European Medicines Agency (EMA), the Heads of Medicines Agency (HMA) and the FDA, standard of care administered to patients differed by institution. In order to ensure balance of standard treatment regimens in both treatment arms, randomization was determined at the individual site level.

Four independent data safety monitoring board (DSMB) recommendations to continue the study were received following three unblinded safety reviews and an unblinded futility analysis. be convened for the safety oversight of the study in order to assuring safety of the trial participants.

Stratification:

Patients were stratified based on meeting three or more high risk clinical parameters for COVID-19 outcomes at baseline (yes or no). The parameters were: 1) age at screening, ≥60 years of age, (yes or no); 2) male, (yes or no); 3) HbA1c at screening, ≥6.5 (yes or no); 4) hypoxemia without commensurate increased work of breathing (defined as increased respiratory rate, nasal flaring and/or increase use of respiratory muscles including the diaphragm [yes or no]; 5) known underlying chronic lung disease (yes or no); 6) known cardiovascular disease or hypertension (yes or no); 7) BMI≥28.0 kg/m$^2$ (yes or no); 8) known renal disease (yes or no).

Treatment and Administration:

Opaganib 500 mg Q12 hour or matching placebo. Opaganib or placebo made into a suspension form could be administered by nasogastric tube.

Study Duration:

The maximum duration of study participation was up to 45 days (including up to 3 days screening; up to 14 days of double-blind treatment and 28 days off-study drug follow-up).

Eligibility Criteria:

Inclusion:
1. Adult male or female≥18 to ≤80 years of age
2. Proven COVID-19 infection per RT-PCR assay of a pharyngeal sample (nasopharyngeal or oropharyngeal) AND pneumonia defined as radiographic opacities on chest X-ray or CT scan
3. The patient requires, at baseline, high flow supplemental oxygen or CPAP, if high oxygen flow is not an available option (WHO Ordinal Scale 5 at baseline).
4. Patient agrees to use appropriate methods of contraception during the study and 3 months after the last dose of study drug
5. The patient or legal representative has signed a written informed consent approved by the IRB/Ethics Committee Exclusion:
1. Any co-morbidity that may add risk to the treatment in the judgement of the investigator.
2. Requiring intubation and mechanical ventilation
3. Oxygen saturation≥95% on room air
4. Any preexisting respiratory condition that requires intermittent or continuous ambulatory oxygen prior to hospitalization
5. Patient is, in the investigator's clinical judgement, unlikely to survive >72 hours
6. Pregnant (positive serum or urine test within 3 days prior to randomization) or nursing women.
7. Unwillingness or inability to comply with procedures required in this protocol.
8. Corrected QT (QTc) interval on electrocardiogram (ECG) >470 ms for females or >450 ms for males, calculated using Friedericia's formula (QTcF)
9. AST (SGOT) or ALT (SGPT) >2.5× upper limit of normal (ULN)
10. Total bilirubin>1.5×ULN (except where bilirubin increase is due to Gilbert's Syndrome)
11. Serum creatinine>2.0×ULN
12. Absolute neutrophil count<1000 cells/mm$^3$
13. Platelet count<75,000/mm$^3$
14. Hemoglobin<8.0 g/dL
15. Currently taking medications that are sensitive CYP3A4, CYP2C9 or CYP2C19 substrates and have a narrow therapeutic index 16. Currently taking medications that are strong inducers or inhibitors of CYP2D6 and CYP3A4
17. Currently taking warfarin, apixaban, argatroban or rivaroxaban due to drug-drug interaction based on CYP450 metabolism
18. Current drug or alcohol abuse
19. Currently participating in a clinical study assessing pharmacological treatments, including anti-viral studies Screening/Baseline Assessments:
   Signed informed consent by patient or legal representative
   Eligibility determination
   Complete medical history (including onset of COVID-19 symptoms)
   Concomitant medication assessment
   Baseline review of systems
   Physical examination
   Vital signs (temperature, blood pressure, pulse rate, respiratory rate and oxygen saturation by pulse oximeter)
   Weight if the patient is ambulatory
   Oxygen requirement (L/min)
   FiO2 (estimate)
   12-lead electrocardiogram
   Chest Xray or CT scan
   Nasopharyngeal or oropharyngeal swab for SARS-CoV-2 PCR test
   Serum chemistry
   CRP, D-Dimer, LDH, ferritin, cardiac troponin
   HbA1c
   CBC with differential
   Urinalysis
   Serum or urine pregnancy test (for women of childbearing potential) within 3 days prior to treatment Study Assessments:
The following were monitored and documented daily as part of the standard of care:
   Concomitant medications
   Adverse Events
   Interim Physical exam
   Vital signs (temperature, blood pressure, pulse rate, respiratory rate and oxygen saturation by pulse oximeter)
   Oxygen flow rate setting (l/min)
   FiO2 (estimate or known if patient is ventilated)

The following was monitored less frequently as part of standard of care and wherever possible:
   For patients on concomitant chloroquine/hydroxychloroquine/mefloquine, a 12-lead electrocardiogram (if allowed by hospital treatment guidelines under COVID-19) approximately 3 hours after the first study drug administration on Day 1, anytime on Days 2 and 4, and again at end-of-treatment (either Day 14 or at premature study drug discontinuation). If patients were on monitors (including telemetry or Holter monitors), investigators were encouraged to collect QT interval data
   Nasopharyngeal or oropharyngeal viral swab for SARS-CoV-2 PCR test every 3 days
   Serum chemistry once weekly
   Serum CRP, D-Dimer, LDH, ferritin, cardiac troponin once weekly
   CBC with differential once weekly
   Chest X-ray or CT scan as per physician decision Study Endpoints:
Primary
The percentage of patients requiring intubation and mechanical ventilation by Day 14
Secondary
1) The percentage of patients with ≥2 category improvement on the WHO Ordinal Scale for Clinical Improvement
2) The time to intubation and mechanical ventilation
3) The time to low oxygen flow via nasal cannula e.g. from high oxygen flow via nasal cannula or CPAP, if high oxygen flow was not an available option
4) The percentage of patients no longer receiving supplemental oxygen for at least 24 hours by Day 14
5) The total oxygen requirement (area under the curve) using the daily supplemental oxygen flow (L/min) over 14 days (Day 1 to Day 14)
6) The time to two consecutive negative swabs for SARS-CoV-2 by PCR, at least 24 hours apart
7) The percentage of patients with at least two consecutive negative swabs for SARS-CoV-2 by PCR at Day 14
8) The percentage of patients with at least one measurement of fever at baseline (defined as temperature>38.0 C [100.4 F]), who are afebrile (defined as temperature<37.2 C [99 F]) at Day 14
9) Mortality due to any cause at Day 30 after baseline
Exploratory
The mean change in systemic markers of inflammation (D-dimer, cardiac troponin, C-reactive protein [CRP], procalcitonin [PCT], lactate dehydrogenase [LDH] and ferritin) from baseline at Day 14
Safety
1) Incidence rates of all treatment-emergent AEs (TEAEs) and SAEs
2) Evaluation of vital signs
3) Evaluation of laboratory parameters (chemistry and hematology)
4) Evaluation of electrocardiograms (ECG)

Prohibited Medications During the Study:
The following medications were prohibited during the study, including the 28-day follow-up period:
   Medications that are sensitive CYP3A4, CYP2C9 or CYP2C19 substrates and have a narrow therapeutic index were prohibited
   Strong inducers or inhibitors of CYP2D6 and 3A4 were prohibited
Warfarin, apixaban, argatroban and rivaroxaban were prohibited due to drug-drug interaction based on CYP450 metabolism Stopping Rules:
At any time during the study, participants stopped study drug if it was determined that they have experienced any of the following adverse events (using Grading criteria as defined in the revised NCI Common Terminology for Adverse Events [CTCAE v.5.0])
   Any neuropsychiatric adverse event of Grade 3 severity
   Hallucinations of any severity (any Grade)
   Nausea of Grade 3 severity
   Vomiting of Grade 3 severity
   Creatinine increase of Grade 2 severity Statistical Methods:
The primary analysis was based on a composite failure (Yes/No) variable, indicating if a subject had required intubation and mechanical ventilation or had died by study Day 14.

In the rare case of unknown patient outcome (patient lost to follow up), it was also counted as treatment failure for the primary analysis. If a patient initiated new investigational therapy for COVID-19 within 14 days, this was also regarded, in the primary analysis, as treatment failure.

The number and percentages of subjects with failure event was tabulated per treatment group. A 95% confidence interval was constructed for each proportion. A Cochran Mantel- Haenzel (CMH) test compared the proportion of failure between the two groups, using the study stratification factors used for randomization, and corresponding risk difference estimate presented with 95% confidence interval. Exact confidence intervals were used as needed.

The significance level for this test was two-sided 5%. In the case of small number of events (less than 5 events in any study arm), the Fisher exact test was used.

The number and percent of each of the failure types (intubation and mechanical ventilation was described by group.

The primary analysis was based on the modified Intent to treat population (mITT), which consisted of all patients that were randomized and treated with at least one dose of study drug. Analysis demonstrated a compelling benefit of opaganib in the 'moderately severe' patients in the study:

These were 251/463 subjects (54% of mITT) requiring Fraction of inspired Oxygen (FiO2) up to and including 60% at baseline (median FiO2)

These patients represent the lower half of the study's population in terms of oxygen requirement & disease severity (based on the median)

This covers all the low-flow patients (WHO Ordinal Scale 4) and approximately half of the high-flow patients (WHO Ordinal Scale 5)—together these are the vast majority of hospitalized COVID-19 patients Consistent with prior U.S. Phase 2 study results presented in Example 4 (majority of low flow patients) and opaganib's anti-viral effect, the FiO2 up to 60% parameter is highly informative for directing opaganib to this patient population that stands to significantly benefit from the treatment and represents a paradigm changing approach to classifying disease severity in COVID-19.

Figure 7:
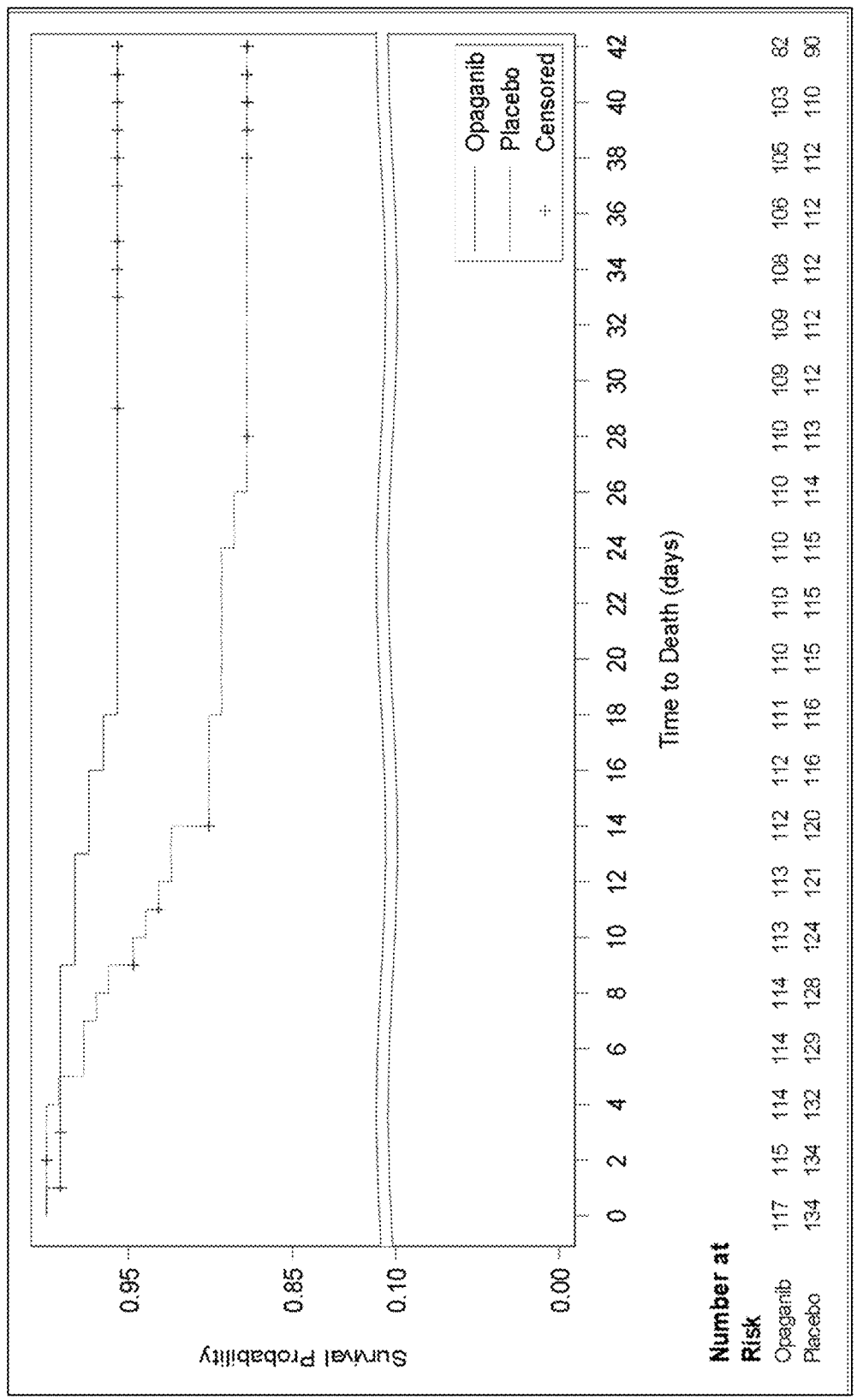
FIG. 7 shows a Kaplan-Meier curve of time to death through end of follow-up (Day 42) for mITT with baseline $FiO_2 \leq 60\%$ post statistical analysis from the randomized, double-blind, placebo-controlled Phase 2/3 study of opaganib in COVID-19 pneumonia described in Example 5.

Mortality: Opaganib treatment resulted in a significant 62% reduction in mortality (7/117 patients treated with opaganib vs. 21/134 for placebo; nominal p-value=0.019, Relative Risk 2.6) (Sensitivity Analysis: 5/117 vs. 16/134, a significant 64% efficacy benefit; nominal p-value=0.033, Relative Risk—2.8), see FIG. 7

Reaching Room Air by Day 14 (primary endpoint of the study): 90/117 (77%) of opaganib-treated patients reached room air by Day 14 vs. 85/134 (63.5%) for placebo—a significant efficacy benefit of 21% with opaganib (nominal p-value=0.033 by Cochran Mantel-Haenzel test using the study stratification factors used for randomization, and corresponding stratified proportion difference with 95% CI). (No longer received supplemental oxygen for at least 24 hours by Day 14)

Figure 8:
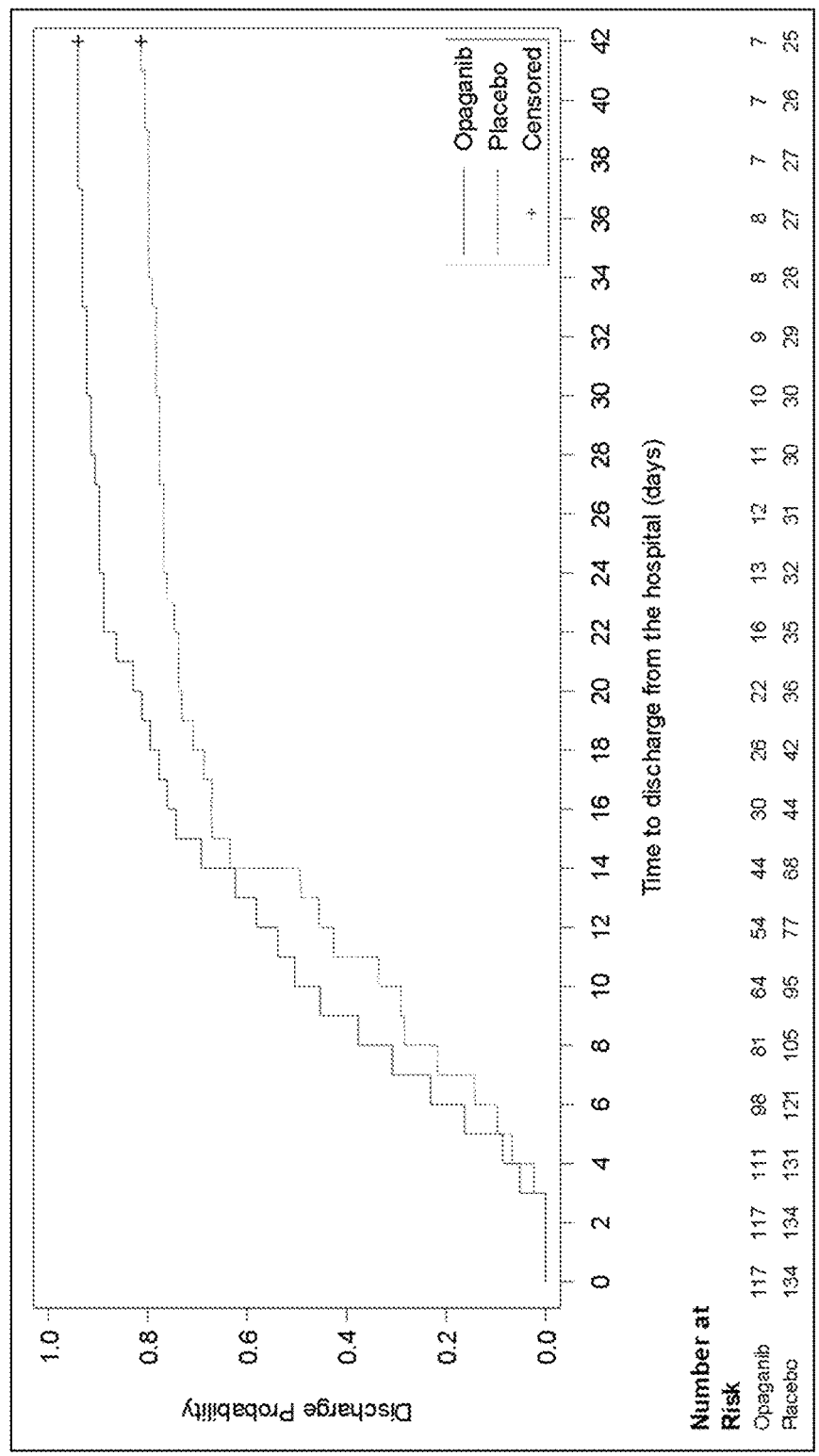
FIG. 8 shows a Kaplan-Meier curve of median time to discharge which was 4 days shorter with opaganib vs. placebo (10 vs. 14) (251 patients from the study mITT population with baseline $FiO_2 \leq 60\%$) post statistical analysis from the randomized, double-blind, placebo-controlled Phase 2/3 study of opaganib in COVID-19 pneumonia described in Example 5.

Median time to discharge: Patients treated with opaganib showed median time of 10 days to discharge vs. 14 days for the placebo arm, resulting in a significant saving of four days hospitalization per opaganib patient (nominal p-value=0.0195), see FIG. 8.

Safety: Overall adverse events were balanced between the opaganib and placebo groups, suggesting good safety, with no new safety signals emerging

TABLE 5

Benefit observed across secondary endpoints with nominally significant p-values:

| Parameter | Statistics | Opaganib (N = 117) | Placebo (N = 134) | Outcome |
|---|---|---|---|---|
| Patients With an Improvement of 2 or More on the WHO Ordinal Scale Compared to Baseline by Day 14* | n (%) | 93 (79.49) | 88 (65.67) | |
| Difference in Rates (Opaganib-Placebo) | % | | | 13.82 |
| | p-value** | | | 0.023 |
| Time to a score of <=3 on the WHO Ordinal Scale | | | | |
| Number of Events | n (%) | 93 (79.5) | 88 (65.7) | |
| Kaplan-Meier Median (days) | Estimate 95% CI | 8.00 (7.00-9.00) | 10.00 (9.00-12.00) | |
| | p-value** | | | 0.010 |
| Time to Discharge by day 42 | | | | |
| Number of Events (%) | n (%) | 81 (69.2) | 85 (63.4) | |
| Restricted Mean Analysis | p-value | | | 0.0022 |
| Kaplan-Meier Mean (days) | Estimate | 13.41 | 17.89 | |
| Difference (days) and 95% CI | | | | -4.48 (-7.34, -1.62) |

*Analysis statistics were estimated using Log Rank test stratified by study stratification factors used for randomization. A negative (positive) statistic is associated with longer (shorter) time to the event

**p-value from Cochran Mantel-Haenzel test using the study stratification factors used for randomization, and corresponding stratified proportion difference with 95% CI Evaluation of baseline biomarkers supports the use of FiO2 as indicator of disease severity and as a predictor of the treatment benefit in the target population.

TABLE 6

Biomarker medians by subpopulations (FiO2 ≤ 60% and FiO2 ≥ 60% at baseline)

| Marker | Lower FiO2 | | | Higher FiO2 | | | p-value* |
|---|---|---|---|---|---|---|---|
| | N | Median | Q1, Q3 | N | Median | Q1, Q3 | |
| Lymphocytes ($10^9$/L) | 246 | 0.990 | 0.70, 1.38 | 178 | 0.780 | 0.50, 1.16 | <.0001 |
| C Reactive Protein (mg/L) | 240 | 60.800 | 21.40, 153.40 | 186 | 102.800 | 38.67, 200.30 | 0.0005 |
| Ferritin (μg/L) | 228 | 666.950 | 370.17, 1297.50 | 167 | 1000.000 | 500.60, 2000.00 | 0.0008 |
| D-Dimer (μg/ml) | 240 | 0.450 | 0.18, 1.06 | 178 | 0.806 | 0.31, 1.79 | 0.0004 |
| Lactate Dehydrogenase (IU/L) | 230 | 361.150 | 290.60, 522.00 | 183 | 469.230 | 344.00, 644.00 | <.0001 |
| Troponin T (μg/L) | 44 | 0.009 | 0.00, 0.06 | 60 | 0.010 | 0.01, 0.02 | 0.1616 |

*Comparing opaganib vs. placebo arms for imbalances

The post-hoc analysis is robust, rigorous and adheres to strict standards of integrity and reliability. FiO2 is a clinically and medically relevant parameter for oxygen requirement and disease severity, irrespective of the device providing the oxygen. The cutoff selected of FiO2 up to 60% was objectively based on the median of the distribution of FiO2 levels globally across the entire study and across a wide range of oxygen supplementation devices. Potential cofounding factors were rigorously analyzed—negating potential impact of baseline risk-factors and SOC on the outcome. Territorial variability was analyzed—showing robust consistency.

INDUSTRIAL APPLICABILITY

The present invention provides an anti-coronavirus agent comprising as an active ingredient a compound represented by:

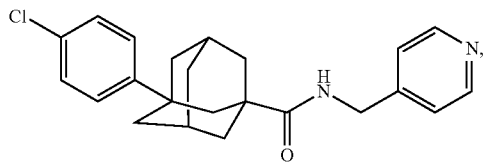 [SMILES: O=C(NCc1ccncc1)C12CC3CC(C1)CC(c1ccc(Cl)cc1)(C3)C2]

as a freebase or as a salt thereof, an anti-SARS agent comprising the anti-coronavirus agent and a method of treating SARS using the anti-coronavirus agent. The present invention enables the treatment of diseases caused by coronaviruses, especially the SARS-associated coronavirus.

All patents, patent applications, and published references cited herein are hereby incorporated by reference in their entirety. Various modifications and variations of the described compositions and methods of the invention will be apparent to those skilled in the art without departing from the scope and spirit of the invention. Although the invention has been described in connection with specific embodiments, it will be understood that the invention should not be unduly limited to such specific embodiments. Indeed, various modifications of the described modes for carrying out the invention that are obvious to those skilled in the fields of molecular biology, medicine, immunology, pharmacology, virology, or related fields are intended to be within the scope of the invention.

What is claimed is:

1. A method for the inhibition of a disease caused by a coronavirus, the method comprising:
   confirming that a patient is infected with a coronavirus and also has pneumonia, wherein the patient receives a supplemental oxygen at a fraction of inspired oxygen (FiO2) up to and including 60%; and
   administering to the patient an effective amount of ABC294640,

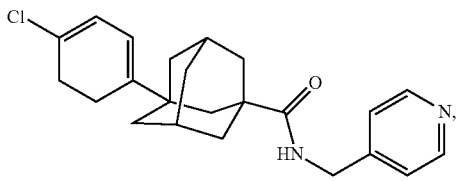 [SMILES: O=C(NCc1ccncc1)C12CC3CC(C1)CC(C1=CC=C(Cl)CC1)(C3)C2]

as a free base or salt thereof.

2. The method of claim 1, wherein the ABC294640 is in the form of is hydrochloride salt.

3. The method of claim 2, further comprising a pharmaceutically-acceptable carrier material, wherein the ABC294640 hydrochloride and the pharmaceutically-acceptable carrier material are in a unit dosage form suitable for oral administration.

4. The method of claim 3, wherein the unit dosage form is a solid dosage form.

5. The method of claim 4, wherein the solid dosage form is a capsule.

6. The method of claim 1, wherein the patient is receiving supplemental oxygen via nasal cannula.

7. The method of claim 1, wherein the patient is receiving supplemental oxygen via face mask.

8. The method of claim 1, wherein the coronavirus is a respiratory syndrome coronavirus.

9. The method of claim 8, wherein the respiratory syndrome coronavirus is a severe acute respiratory syndrome coronavirus (SARS).

10. The method of claim 9 wherein the severe acute respiratory syndrome coronavirus is severe acute respiratory syndrome coronavirus-2 (SARS-CoV-2).

11. The method of claim 10, wherein the SARS-CoV-2 virus is a naturally occurring coronavirus.

12. The method of claim 10, wherein the SARS-CoV-2 virus is a naturally occurring coronavirus variant.

13. The method of claim 3, wherein the unit dosage form suitable for oral administration is a capsule having 250 mg of ABC294640 hydrochloride, and wherein administering includes two capsules administered twice a day, for at least 10 days, for a total daily dose of 1000 mg of ABC294640 hydrochloride.

14. The method of claim 2, further comprising a pharmaceutically-acceptable carrier material, wherein the pharmaceutically-acceptable carrier material is physiologically buffered saline.

15. The method of claim 14, wherein a suspension is formed that includes ABC294640 hydrochloride suspended in physiologically buffered saline, and wherein the administering includes using a tube to deliver the suspension directly to the stomach.

16. The method of claim 1, further comprising co-administering to the patient at least one additional antiviral active agent.

17. The method of claim 16, wherein the antiviral active agent is a nucleotide-analog anti-viral prodrug.

18. The method of claim 17, wherein the nucleotide-analog anti-viral prodrug is Remdesivir.

19. The method of claim 5, further comprising co-administering to the patient at least one additional antiviral active agent.

20. The method of claim 19, wherein the antiviral active agent is a nucleotide-analog anti-viral prodrug.

\* \* \* \* \*